US012616851B2

(12) United States Patent
Hakala et al.

(10) Patent No.: US 12,616,851 B2
(45) Date of Patent: May 5, 2026

(54) TWO-STEP BEAM GEOMETRY OPTIMIZATION AND BEAM ENTRY ANGLES WITHOUT ISOCENTER

(71) Applicant: Siemens Healthineers International AG, Steinhausen (CH)

(72) Inventors: Mikko Hakala, Rajamäki (FI); Shahab Basiri, Siuntio (FI); Kellee Donnelly, Helsinki (FI); Elena Czeizler, Helsinki (FI); Esa Kuusela, Espoo (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 209 days.

(21) Appl. No.: 18/367,860

(22) Filed: Sep. 13, 2023

(65) Prior Publication Data

US 2025/0082964 A1 Mar. 13, 2025

(51) Int. Cl.
*A61N 5/10* (2006.01)
*G16H 20/40* (2018.01)

(52) U.S. Cl.
CPC ......... *A61N 5/1031* (2013.01); *A61N 5/1038* (2013.01); *A61N 5/1045* (2013.01); *A61N 5/1065* (2013.01); *A61N 5/1069* (2013.01); *A61N 5/1081* (2013.01); *G16H 20/40* (2018.01); *A61N 2005/1034* (2013.01); *A61N 2005/1035* (2013.01)

(58) Field of Classification Search
None
See application file for complete search history.

(56) References Cited

U.S. PATENT DOCUMENTS

| | | | |
|---|---|---|---|
| 6,546,073 B1 | 4/2003 | Lee | |
| 6,741,674 B2 | 5/2004 | Lee | |
| 9,044,602 B2 | 6/2015 | Kilby et al. | |
| 2004/0165696 A1 * | 8/2004 | Lee ........................ | G16H 20/40 378/65 |
| 2009/0060130 A1 | 3/2009 | Wilkens et al. | |
| 2010/0020931 A1 | 1/2010 | Otto et al. | |
| 2010/0054411 A1 | 3/2010 | Nord et al. | |
| 2010/0104068 A1 * | 4/2010 | Kilby ................... | A61N 5/1031 378/65 |
| 2015/0094515 A1 | 4/2015 | Witten et al. | |

(Continued)

FOREIGN PATENT DOCUMENTS

CN 115620870 A 1/2023

OTHER PUBLICATIONS

European Search Report and European Search Opinion issued Jan. 23, 2025, in European Patent Application No. 24197341.1.

(Continued)

*Primary Examiner* — Marcus H Taningco
(74) *Attorney, Agent, or Firm* — Potomac Law Group, PLLC

(57) ABSTRACT

Systems and methods are disclosed for optimizing a treatment plan using all degrees of freedom including those related to beam geometry parameters, the optimization including a step for limiting the search space for the beam geometry parameters using a trained machine learning model, and systems and methods are disclosed for obtaining beam geometry parameters for treatment planning that do not require knowledge of the beam delivery device isocenter.

20 Claims, 13 Drawing Sheets

(56)        References Cited

U.S. PATENT DOCUMENTS

| | | | |
|---|---|---|---|
| 2018/0111005 A1 | 4/2018 | Ranganathan et al. | |
| 2019/0038916 A1* | 2/2019 | Ranganathan et al. | |
| 2020/0178890 A1* | 6/2020 | Otto .................... | A61N 5/1082 |
| 2020/0206533 A1 | 7/2020 | Laaksonen et al. | |
| 2020/0282237 A1 | 9/2020 | Nord et al. | |
| 2020/0286601 A1* | 9/2020 | Khuntia ................ | G16H 80/00 |
| 2020/0353286 A1 | 11/2020 | Wu et al. | |
| 2021/0065360 A1 | 3/2021 | Laaksonen et al. | |
| 2021/0069527 A1 | 3/2021 | Peltola et al. | |
| 2021/0178189 A1 | 6/2021 | Locke et al. | |
| 2021/0304866 A1 | 9/2021 | Kuusela et al. | |
| 2021/0379404 A1 | 12/2021 | Basiri et al. | |
| 2021/0387018 A1 | 12/2021 | Hakala et al. | |
| 2022/0008748 A1* | 1/2022 | Huang ................ | A61N 5/1077 |
| 2022/0088411 A1 | 3/2022 | Kauppinen et al. | |
| 2022/0093242 A1 | 3/2022 | Hakala et al. | |
| 2022/0387821 A1* | 12/2022 | Zhao .................... | A61N 5/1031 |
| 2022/0414525 A1 | 12/2022 | Princ et al. | |
| 2023/0087944 A1 | 3/2023 | Hakala et al. | |

OTHER PUBLICATIONS

Unkelbach et al., Optimization approaches to volumetric modulated arc therapy planning, Med. Phys. 42(3), Mar. 2015.
Field et al., "Machine learning applications in radiation oncology", Phys Imaging Radiat Oncol, Jul. 2021, 19:13-24.
Partial European Search Report and European Provisional Opinion issued Oct. 30, 2024, in European Patent Application No. 24197341.1.

* cited by examiner

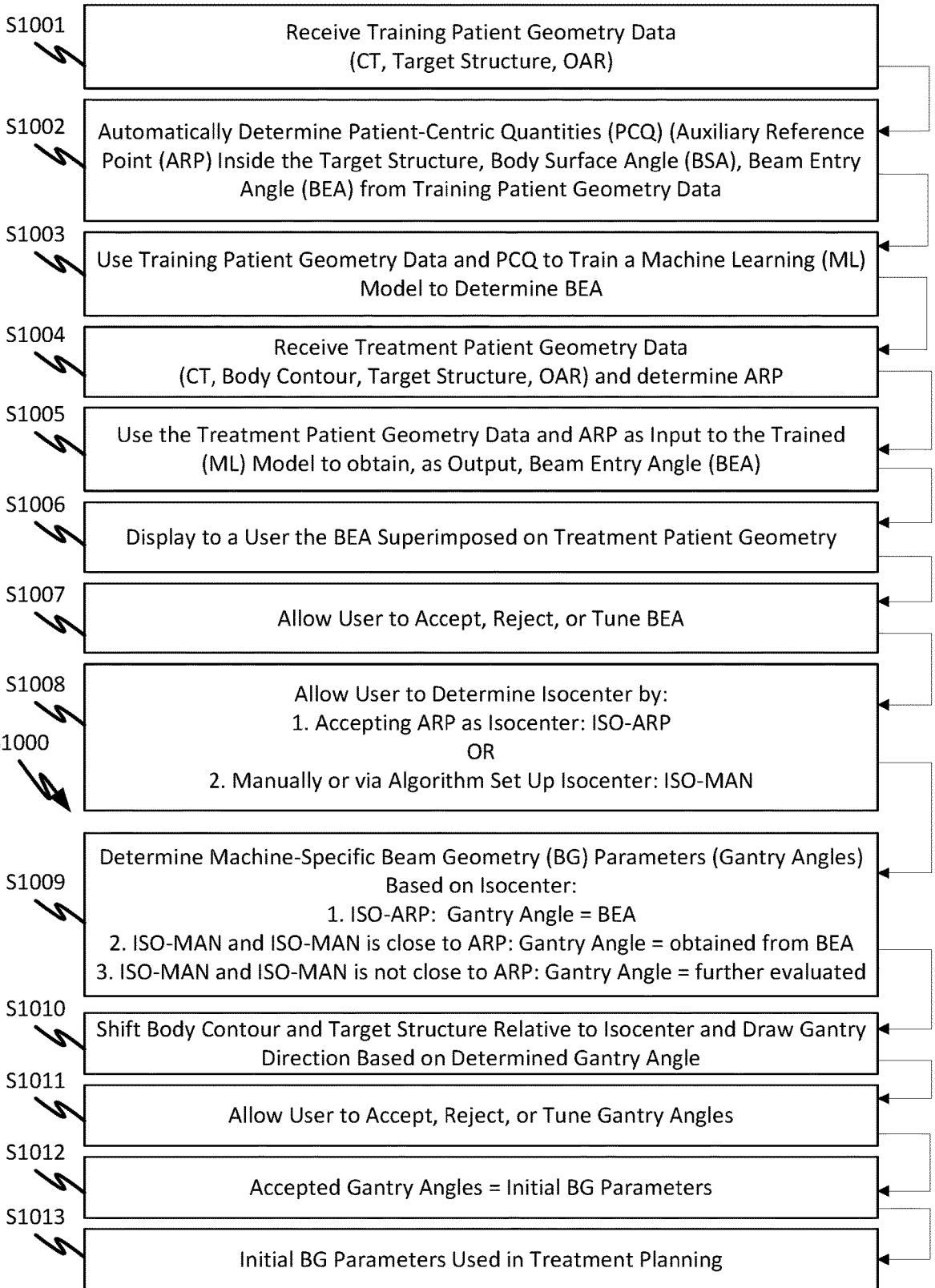

S1001 — Receive Training Patient Geometry Data (CT, Target Structure, OAR)

S1002 — Automatically Determine Patient-Centric Quantities (PCQ) (Auxiliary Reference Point (ARP) Inside the Target Structure, Body Surface Angle (BSA), Beam Entry Angle (BEA) from Training Patient Geometry Data S1003 — Use Training Patient Geometry Data and PCQ to Train a Machine Learning (ML) Model to Determine BEA S1004 — Receive Treatment Patient Geometry Data (CT, Body Contour, Target Structure, OAR) and determine ARP S1005 — Use the Treatment Patient Geometry Data and ARP as Input to the Trained (ML) Model to obtain, as Output, Beam Entry Angle (BEA)

S1006 — Display to a User the BEA Superimposed on Treatment Patient Geometry

S1007 — Allow User to Accept, Reject, or Tune BEA

S1008 — Allow User to Determine Isocenter by:
1. Accepting ARP as Isocenter: ISO-ARP
OR
2. Manually or via Algorithm Set Up Isocenter: ISO-MAN

S1000

S1009 — Determine Machine-Specific Beam Geometry (BG) Parameters (Gantry Angles) Based on Isocenter:
1. ISO-ARP: Gantry Angle = BEA
2. ISO-MAN and ISO-MAN is close to ARP: Gantry Angle = obtained from BEA
3. ISO-MAN and ISO-MAN is not close to ARP: Gantry Angle = further evaluated S1010 — Shift Body Contour and Target Structure Relative to Isocenter and Draw Gantry Direction Based on Determined Gantry Angle S1011 — Allow User to Accept, Reject, or Tune Gantry Angles S1012 — Accepted Gantry Angles = Initial BG Parameters S1013 — Initial BG Parameters Used in Treatment Planning

TWO-STEP BEAM GEOMETRY OPTIMIZATION AND BEAM ENTRY ANGLES WITHOUT ISOCENTER

FIELD

The present disclosure relates generally to treatment plan optimization processes and generating beam geometry (BG) solutions for treatment plans, and more particularly, to systems, methods, and devices for automated treatment plan optimization processes having all degrees of freedom including those related to beam geometry (BG) parameters, and to systems, methods, and devices for generating beam geometry (BG) solutions without having to define the iso-center of the external radiation beam delivery system.

BACKGROUND

Radiation therapy involves medical procedures that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy, while minimizing radiation exposure to the surrounding tissue and critical anatomical structures.

In general, a full radiotherapy planning and treatment workflow includes several phases: a treatment planning phase, a treatment delivery phase, and a monitoring and evaluating phase in which the progress of the treatment, e.g., the dose accumulation is monitored. The treatment delivery phase generally overlaps with the monitoring and evaluation phase. Treatment is generally delivered in many sessions, which span several weeks. The patient is monitored throughout the duration of the treatment to evaluate the progress of treatment and whether there is any need to re-plan or adapt the treatment.

In the treatment planning phase, first a precise three-dimensional (3D) map of the anatomical structures in the area of interest (head, body, etc.) is constructed using any one of (or combinations thereof) a computed tomography (CT), cone-beam computed tomography (CBCT), magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. On these images, organs at risk (OARs) in the region of interest are also delineated. This is followed by a prescription step, where the level of radiation which should be delivered to the target (tumors) and the level of protection of the OARs which needs to be achieved to avoid side-effects for the patient is specified. In the prescription step, a motion path for the radiation beam is also computed to deliver a dose distribution to the target within a treatment volume that the radiation oncologist finds acceptable, considering a variety of medical constraints. Then, a team of specialists develop a treatment plan using special computer software to optimally irradiate the tumor and minimize dose to the surrounding normal tissue by designing beams of radiation to converge on the target area from different angles and planes.

In the treatment delivery phase, the radiation treatment plan is executed. During this phase, the radiation dose is delivered to the patient according to the prescribed treatment plan. Generally, a treatment plan is delivered to the patient over a series of radiation treatments referred to as fractions. There are many factors, however, such as, differences in a patient's setup position, changes that might occur if a patient's tumor regresses or if the patient loses weight during therapy, and uncertainties introduced by motion, for example, that can contribute to differences between the prescribed radiation dose distribution and the actual dose delivered (i.e., the actual dose delivered to the target during the radiation treatment). These anatomical and physiological changes can cause the target volumes and surrounding anatomical structures and organs to move and change in size and shape during the therapy. As such, executing or continuing to execute the initial treatment plan may result in an actual received dose distribution that differs from the planned distribution, and thus reduced doses to target volumes and/or increased doses to organs at risk (OARs). During the treatment delivery phase, therefore, the treatment plan may be adapted to the image of the day to better reflect the current situation. This involves making modifications to the initial treatment plan to match the new location and shape of the target volume and surrounding anatomical structures based on subsequently acquired image data.

Generating an optimal treatment plan, whether it is the initial treatment plan generated during the treatment planning phase, or the adapted plan generated during the treatment delivery phase of an adaptive treatment workflow, can be time consuming and tedious, especially in the field of intensity modulated radiation therapy (IMRT) and volumetric-modulated arc therapy (VMAT) where complex matrix manipulations are required for generating and optimizing treatment plans. The complexity and duration of the treatment planning phase also comes from the fact that the optimization step may need to be repeated several times after modifying one or more parameters including field geometry parameters (i.e., isocenter position, number of fields, position of fields, size of the fields for VMAT arcs, etc.) and/or optimization parameters (i.e., objectives, priorities, etc.).

Optimization is an iterative process where the user attempts to specify planning goals in the form of dose or biological objectives to create an ideal dose to the target (tumor) and minimize the dose to critical structures (i.e., organs at risk OARs). During optimization, the dose distribution within the treatment volume is evaluated at each iteration until a satisfactory dose distribution is obtained.

Generally, in IMRT and VMAT, creating an optimal treatment plan involves solving the inverse problem of determining optimal combination of angles, radiation doses and multi-leaf collimator (MLC) leaf movements to deliver the desired total radiation dose to the target while minimizing irradiation of the healthy tissue. This may be reduced to an objective function that accounts for the relative importance of various trade-offs inherent in such a plan along with constraints that must be met for the plan to be medically acceptable or physically possible. To create a deliverable treatment plan, treatment planning algorithms must account for the capabilities of the specific radiation therapy system they are used with.

Current optimization algorithms use dose-volume objectives to guide the search for the system parameters, as the quality of the generated plan depends on the choice of these objectives. In general, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. The process is performed iteratively until an optimized plan is reached.

However, the search space for system parameters are generally too large for an optimizer to work with. Therefore, in current IMRT and VMAT optimization algorithms, the beam geometry (BG) (i.e., machine instructions, such as, gantry angles, collimator angles, and other variable system parameters associated with the radiation therapy system, excluding MLC leaf and jaw positions) is either not being considered as an optimization objective (i.e., BG parameters are not optimized) or, when it is considered as an optimization objective, the optimization algorithm produces beam geometries that are not acceptable (i.e., obtained BG parameters are too complex to be implemented in practical applications or the BG parameters are not clinically acceptable).

For example, in typical IMRT and VMAT optimization algorithms, instead of iteratively searching for optimal beam geometries, the beam geometry (BG) parameters are fixed prior to treatment plan optimization. This is generally done by using a clinical template specifying the BG parameters, or by a user manually entering the BG parameters. Since the BG parameters are fixed prior to the optimization process, there is no quantity related to the beam geometries that can be optimized during the optimization process.

In knowledge-based approaches to the treatment planning process, machine learning or other inference methods are used to predict beam geometries based on the patient geometry relative to the prior similar patient geometries. The resulting beam geometries, however, are beam geometries that may be useful to a user to pick the beam geometries for manual entry but are not beam geometries that are optimized during the optimization process.

In other approaches to the treatment planning process that include dosimetric aspects, optimization algorithms that include beam trajectory or other beam geometries as optimization objectives either require extensive manually coded rule sets to avoid obtaining too complex or otherwise unfeasible beam geometries, or the optimization process takes a significantly longer time than the standard IMRT optimization process and is therefore not feasible to apply, or the optimization process produces beam geometries that are clinically not acceptable.

In yet other approaches where the beam geometry, such as the collimator angle, is considered an optimization objective, the optimization algorithm does not include dosimetric aspects.

Thus, beam geometry (BG) parameters in current treatment plan optimization processes are not optimized to produce dosimetrically best plans for individual patients.

There is thus a need for a system and method for automated treatment plan optimization that can proceed with all degrees of freedom including those related to beam geometry (BG) parameters.

Further, in current processes for determining beam geometry (BG) parameters to be used in treatment planning, prior knowledge of the system isocenter position is required. Isocenter is traditionally fixed by the human planner, or in some cases, by an automated algorithm. Only after the setting of the isocenter can beam geometry (BG) parameters, particularly the gantry angles, be determined by automated solutions. There is thus a strong dependency of the outcome of the automated beam geometry setup on the numerical value of the isocenter, especially if machine learning models are used as automated solutions.

Such a traditional approach forces an evaluator of the automated beam geometry (BG) generating models to assess the radiation field setup values with respect to the system and not with respect to the patient. A patient-centric approach would be a more natural approach, however, since it is aligned with how treatment planners consider the patient geometry when setting up the radiation fields. In current beam geometry (BG) parameter generating models, there is a complex and often unnecessarily narrow dependency of the automated beam geometry (BG) parameters on the isocenter and its numerical value.

There is thus also a need for a system and method that allows for determining automated beam geometry (BG) parameters (i.e., finding BG solutions) that do not require explicit determination of the system isocenter position.

SUMMARY

Systems and methods are disclosed for automated treatment plan optimization processes that can proceed with all degrees of freedom including those related to beam geometry (BG) parameters.

In embodiments, a treatment plan optimization process comprises a first step configured to limit a search space for an optimization objective of an optimization algorithm, the optimization objective being a beam geometry (BG) parameter of the radiation beam delivery system, and a second step configured to optimize the beam geometry (BG) parameter based on the limited search space obtained in the first step.

In embodiments, the first step includes executing a trained machine learning model to predict, based on patient geometry as input, an initial choice for the beam geometry (BG) parameter.

In embodiments, the first step also includes predicting a feasible range for the beam geometry (BG) parameter and/or a largest acceptable deviation from the initial choice for the beam geometry (BG) parameter.

Additionally, or alternatively, in embodiments, the first step includes using templates for the initial set-up of the beam geometry (BG) parameters and applying a set of rules to define the search space around the templates.

Additionally, or alternatively, the first step includes manually entering an initial choice for the for the beam geometry (BG) parameters and associated search boundaries.

In embodiments, the second optimization step includes: receiving, as input to the treatment plan optimization algorithm, information regarding desired dose distribution within a treatment volume of a patient, and treatment parameters including beam geometry (BG) parameters; calculating dose distribution within the treatment volume by executing the treatment plan optimization algorithm; determining whether the calculated dose distribution is within an acceptable threshold of the desired dose distribution; and iteratively modifying one or more of the treatment parameters including the beam geometry (BG) parameters until the calculated dose distribution is within the acceptable threshold or an endpoint has been reached.

In embodiments, the beam geometry (BG) parameter is modified based on the search space obtained in the first step.

Systems and methods are also disclosed for obtaining beam geometry (BG) parameters for treatment planning without explicit determination of an isocenter of a radiation beam delivery system delivering the treatment plan to a target structure within the patient.

In embodiments, the method comprises: determining a reference point within the target structure; obtaining a predicted beam entry angle relative to the reference point by executing a trained machine learning model; displaying the predicted beam entry angle superimposed on the patient geometry for evaluation; allowing a user to accept the predicted beam entry angle or to interactively modify the predicted beam entry angle until an acceptable beam entry angle is obtained; and allowing the user to accept the reference point as the isocenter or manually enter an isocenter.

In embodiments, the accepted beam entry angle is chosen as the beam geometry (BG) parameter when the reference point is accepted as the isocenter, and the beam geometry (BG) parameter is calculated from the accepted beam entry angle when the manually entered isocenter is in close proximity to the reference point.

Systems including a computer processing device configured to execute a sequence of programmed instructions embodied on a computer-readable storage medium, the execution thereof causing the system to execute the method steps disclosed herein, are also disclosed.

A non-transitory computer-readable storage medium upon which is embodied a sequence of programmed instructions for optimizing a radiation treatment plan by executing a first step configured to limit a search space for an optimization objective of an optimization algorithm, the optimization objective being a beam geometry (BG) parameter of the radiation beam delivery system, and executing a second step configured to optimize the beam geometry (BG) parameter based on the limited search space obtained in the first step, and a computer processing system that executes the sequence of programmed instructions embodied on the computer-readable storage medium are also disclosed. Execution of the sequence of programmed instructions can cause the computer processing system to execute the treatment planning and optimization processes described herein.

A non-transitory computer-readable storage medium upon which is embodied a sequence of programmed instructions for obtaining beam geometry (BG) parameters for treatment planning without explicit determination of an isocenter of a radiation beam delivery system delivering the treatment plan to a target structure within the patient, and a computer processing system that executes the sequence of programmed instructions embodied on the computer-readable storage medium are also disclosed. Execution of the sequence of programmed instructions can cause the computer processing system to execute the automated process to obtain machine isocenter independent beam geometry (BG) solutions described herein.

Objects and advantages of embodiments of the disclosed subject matter will become apparent from the following description when considered in conjunction with the accompanying drawings.

BRIEF DESCRIPTION OF DRAWINGS

FIGS. 11-12 are schematic flow diagrams for an automated process to predict beam geometry parameters without explicitly defining a system isocenter.

FIG. 15 is a flow diagram of automated process to predict beam geometry parameters without explicitly defining a system isocenter to be used in treatment planning.

DETAILED DESCRIPTION

Figure 1:
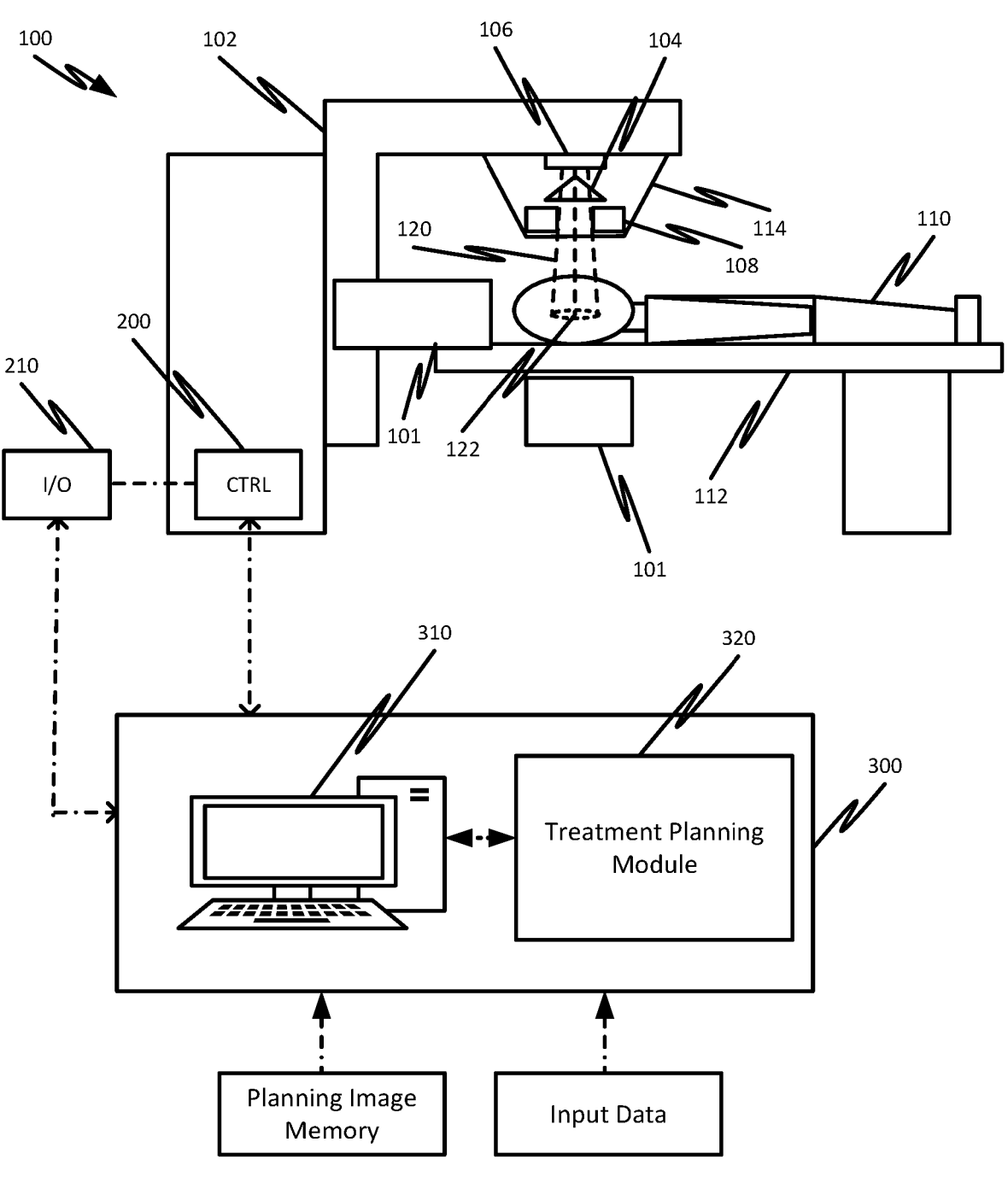
FIG. 1 is a simplified schematic diagram of a radiation therapy system, according to various embodiments of the disclosed subject matter.

Referring to FIG. 1, an exemplary radiation therapy system 100 is shown, which can be used in radiation therapy, and which can deliver radiation in accordance with treatment plans that are determined using techniques described herein. The radiation therapy system 100 can provide radiation to a patient 110 positioned on a treatment couch 112 and can allow for the implementation of various radiation treatment protocols. The radiation therapy can include photon-based radiation therapy, particle therapy, electron beam therapy, or any other type of treatment therapy.

In an embodiment, the radiation therapy system 100 can include a radiation treatment device 101 such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 200.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)). The MLC 108 therefore can be used to provide conformal treatment of tumors from various angles, as well as intensity modulated radiotherapy, whereby different radiation doses are delivered to different portions of the treatment area. The treatment volume, namely, the irradiated volume proximate to the isocenter in the path of the X-ray beam, is defined by the jaws, the head 114, and the MLC 108. In IMRT, the leaves of the MLC are moved so that the treatment volume comprises the volume exposed during the course of the treatment.

Alternatively, or additionally, the radiation therapy device 101 can be a tomotherapy device, a helical tomotherapy device, or a simplified intensity modulated arc therapy (SIMAT) device, a volumetric modulated arc therapy (VMAT) device, or a volumetric high-definition (or hyper-arc) therapy (HDRT). In effect, any type of IMRT device can be employed as the radiation therapy device 101 of system 100, and can also include an on-board volumetric imaging, which can be used to generate in-treatment image data generated during a treatment session.

Each type of radiation therapy device can be accompanied by a corresponding radiation plan and radiation delivery procedure.

The controller 200, which can be, but is not limited to, a graphics processing unit (GPU), can include a computer with appropriate hardware such as a processor, and an operating system for running various software programs and/or communication applications. The controller 200 can include software programs that operate to communicate with the radiation therapy device 101, which software programs are operable to receive data from external software programs and hardware. The computer can also include any suitable input/output (I/O) devices 210, which can be adapted to allow communication between controller 200 and a user of the radiation therapy system 100, e.g., medical personnel. For example, the controller 200 can be provided with I/O interfaces, consoles, storage devices, memory, keyboard, mouse, monitor, printers, scanner, as well as a departmental information system (DIS) such as a communication and management interface (DICOM) for storing and transmitting medical imaging information and related data and enabling the integration of medical imaging devices such as scanners, servers, workstations, printers, network hardware, etc.

Alternatively, or additionally, the I/O devices 210 can provide access to a network (not shown) for transmitting data between controller 200 and remote systems. For example, the controller 200 can be networked via I/O 210 with other computers and radiation therapy systems. The radiation therapy system 100, the radiation treatment device 101, and the controller 200 can communicate with a network as well as databases and servers, for example, a dose calculation server (e.g., distributed dose calculation framework), a treatment planning system 300, a computer processing device for training one or more machine learning models, a computer processing device for applying one or more trained machine learning models, and/or any other data processing computer processing devices. The controller 200 may also be configured to transfer medical image related data between different pieces of medical equipment.

The system 100 can also include a plurality of modules containing programmed instructions (e.g., as part of controller 200, or as separate modules within system 100, or integrated into other components of system 100), which instructions cause system 100 to perform different functions related to radiation therapy including adaptive radiation therapy or other radiation treatment, as discussed herein, when executed. For example, the system 100 can include or communicate with a treatment planning module 320 of a treatment planning system 300 operable to generate the treatment plan for the patient 110 based on a plurality of data input to the system by the medical personnel using computer 310, a patient positioning module operable to position and align the patient 110 with respect to a desired location, such as the isocenter of the gantry, for a particular radiation therapy treatment, an image acquiring module operable to instruct the radiation therapy system and/or the imaging device to acquire images of the patient 110 prior to the radiation therapy treatment (i.e., pre-treatment/reference images used for treatment planning and patient positioning) and/or during the radiation therapy treatment (i.e., in-treatment session images), and to instruct the radiation therapy system 100 and/or the imaging device 101 or other imaging devices or systems to acquire images of the patient 110.

The system 100 can further include one or more contour generation modules operable to generate contours of target volumes and other structures in pre-treatment (planning, reference) and in-treatment (treatment session) images, a contour verification module operable to verify a generated contour, a dose calculation module operable to calculate accumulated dose, a dose evaluation module operable to evaluate dose distribution within a desired volume, modules for electron density map generation, isodose distribution generation, dose volume histogram (DVH) generation, image synchronization, image display, treatment plan generation, treatment plan optimization, automatic optimization parameter generation, updating and selection, and adaptive directives and treatment information transfer. The system 100 can further include a treatment delivery module operable to instruct the radiation therapy device 100 to deliver a treatment plan to the patient 110.

The modules can be written in the C or C++ programming language, for example. Computer program code for carrying out operations as described herein may be written in any programming language, for example, C or C++ programming language.

The treatment planning system 300 can be used to generate optimized treatment plans for the radiation therapy system 100. The treatment planning system 300 includes program memories that contain processor executable instructions that, when executed by the processor 310, generate optimized treatment plans that can be executed by a processing unit (e.g., controller 200) of the radiation therapy system 100. The treatment planning system 300 is configured to communicate with a planning image memory containing image data, and with a knowledge base which is a database or other information retrieval system that contains machine learning models, plan templates including clinical goals (CGs) and priorities for different anatomical structures, as well as knowledge-based information such as patient records (i.e., previous/existing/historical treatment plans) that are similar to the current patient record, treatment types, and knowledge-based statistical models, such as DVH models, for example.

Treatment planning generally starts with obtaining one or more planning images/image slices of the portion of the patient that includes the tumor. The images/image slices may be CT, CBCT, MRI, etc. images/image slices, for example. A qualified medical personnel (physician) next determines and delineates the treatment volume on the image/image slices. Delineating the treatment volume involves generating a body contour around the total volume to be irradiated, as well as delineating the structures contained within the body contour, such as, one or more malignant tumors that are to receive therapeutic doses of radiation (i.e., target structures/volumes) and structures whose irradiation should be limited, since a dose of radiation in excess of a certain amount may adversely affect them (i.e., organs at risk (OARs)). The delineations are generally manually done on the planning image/image slices by the qualified medical personnel (physician), but the contouring may also be performed automatically or semiautomatically using any available segmentation algorithms. The planning images used for the treatment planning can also be images that were previously taken and stored in a planning image memory.

Typical delineations for the malignant tumor include the gross target volume (GTV), the clinical target volume (CTV), and the planning target volume (PTV). The (GTV) determines the anatomic region which harbors the highest tumor cell density and requires the highest prescribed dose. The (GTV) is the position and extent of the gross tumor, i.e., what can be seen, palpated or imaged. The (CTV) contains the (GTV), plus a margin for sub-clinical disease spread which therefore cannot be fully imaged. The (CTV) is the volume that must be adequately treated to achieve cure. The (PTV) allows for uncertainties in planning or treatment delivery. It is a geometric concept designed to ensure that the radiotherapy dose is actually delivered to the (CTV). The (PTV) is thus used to compensate for treatment setup uncertainties through volumetric expansion of the (CTV) margins. Although the treatment volume is a three-dimensional structure including the target volumes and other structures, for ease of illustration, the treatment volume is shown as a two-dimensional cross-sectional structure. This is not to be a limiting feature, however.

Figure 2:
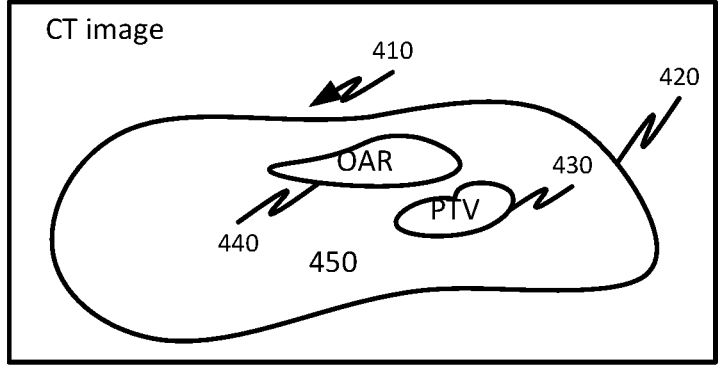
FIG. 2 is a schematic illustration of a treatment volume on a planning image, according to various embodiments of the disclosed subject matter.

FIG. 2 illustrates an exemplary treatment volume 410 including the body contour 420, a target structure/volume (PTV) 430, an OAR 440, as well as the other area 450 of the treatment volume 410 that is not the PTV 430 or the OAR 440 (i.e., the rest of the treatment volume 410, i.e., normal tissue).

After delineating the treatment volume 410, the physician specifies a treatment objective (i.e., treatment prescription), such as a preferred/desired dose distribution within the treatment volume 410. This can be expressed as a set or a template of clinical goals (CG). These clinical goals (CG) can be given, for example, in the form of mean dose of radiation (in Gray) to the target volume 430 and the dose that certain volume of an organ, such as an organ at risk (OAR) 440, or other areas 450 exposed to radiation within the treatment volume 410, must not exceed. Clinical goals, however, may also be given in other dimensions that are not in the form of dose of radiation to a target volume and dose to volume of organ, such as specifying dose values for each voxel within the treatment volume. Voxels represent the three-dimensional rectangular elements that the treatment volume is discretized into. During the treatment, each of these voxels will absorb a dose of radiation.

Each of the given goals can further be ordered in priority describing the importance of meeting a goal in comparison to another goal. Such a set is referred to as a prioritized set of clinical goals (prioritized CG). Each clinical goal can be expressed as a quality metric and its associated goal value. An exemplary prioritized set of clinical goals is:

GOAL 1: Target (PTV) must receive 90 Gy: Priority 1
GOAL 2: Organ at risk (OAR) must receive a max dose of less than 25 Gy: Priority 2

GOAL 3: Other parts of the treatment volume must receive a mean dose of less than 30 Gy: Priority 3.

Another way of expressing desired dose distributions is by employing a library of clinically approved and delivered plans of previously treated patients with similar medical characteristics, in order to find a set of parameters for patient 110 that produces a clinically desirable plan. In this approach, an algorithm (i.e., a Dose Volume Histogram (DVH) model, for example) that has been trained from historical patient data (i.e., structures and dose distributions) is used as a starting point to predict the achievable dose distributions for a new set of patient structures. The achievable dose distributions are presented as a pair of Dose Volume Histograms (DVHs) representing the lower and upper bounds of the 95% confidence interval of the prediction. These DVH histograms can then be used as objectives for each structure within the treatment volume.

The physician also develops a set of treatment parameters, including beam geometry (BG) parameters, to take into account constraints imposed on the treatment process by the radiation therapy system 100 used for delivering the radiation to the treatment volume 410. For example, the physician may need to consider the number of gantry angles and collimator angles needed to deliver the treatment beams at fixed directions (i.e., radiation fields), as well as any other parameters associated with each field, such as, but not limited to, MLC leaf positions, beam intensity profiles, field directions, etc. For this application, beam geometry (BG) parameters include parameters related to machine instructions, including gantry angles, collimator angles, treatment couch angles, isocenter position, etc., but not MLC leaf and jaw positions.

Based on the treatment parameters, a treatment plan is then generated. The generating of a treatment plan generally involves using an algorithm to solve the "inverse problem" of devising and optimizing a specific plan for irradiating the treatment volume 410 from a variety of angles or, in arc therapy, while the gantry is moving, to deliver the desired radiation dose to the target volume while minimizing irradiation of the nearby organs/tissues, etc., while taking into account the capabilities and limitations of the radiotherapy system 100. Thus, treatment planning essentially involves devising a plan to deliver an optimal dose distribution to the treatment volume. This may be reduced to a cost function (objective function) that accounts for various trade-offs inherent in such plans with constraints that must be met for the plan to be medically acceptable or physically possible.

The algorithms that may be used for treatment planning are dose calculation algorithms based on a given set of parameters, such as gantry angle, MLC leaf positions, etc., or search algorithms which use various techniques to adjust the treatment parameters between dose calculations to achieve optimization of the plan. There are many algorithms that can be used for treatment planning. For example, dose calculation algorithms may include, but are not limited to, Monte Carlo techniques, pencil beam convolution, generalized Gaussian pencil beam, collapsed convolution, and anisotropic analytical algorithms. Search algorithms may include various stochastic, deterministic and other methods, including but not limited to, simulated annealing techniques, generalized simulated annealing, dual annealing, swarm-based algorithms, algebraic inverse treatment planning, simultaneous iterative inverse planning, iterative least-square inverse treatment planning, and superposition convolution, for example.

Figure 3:
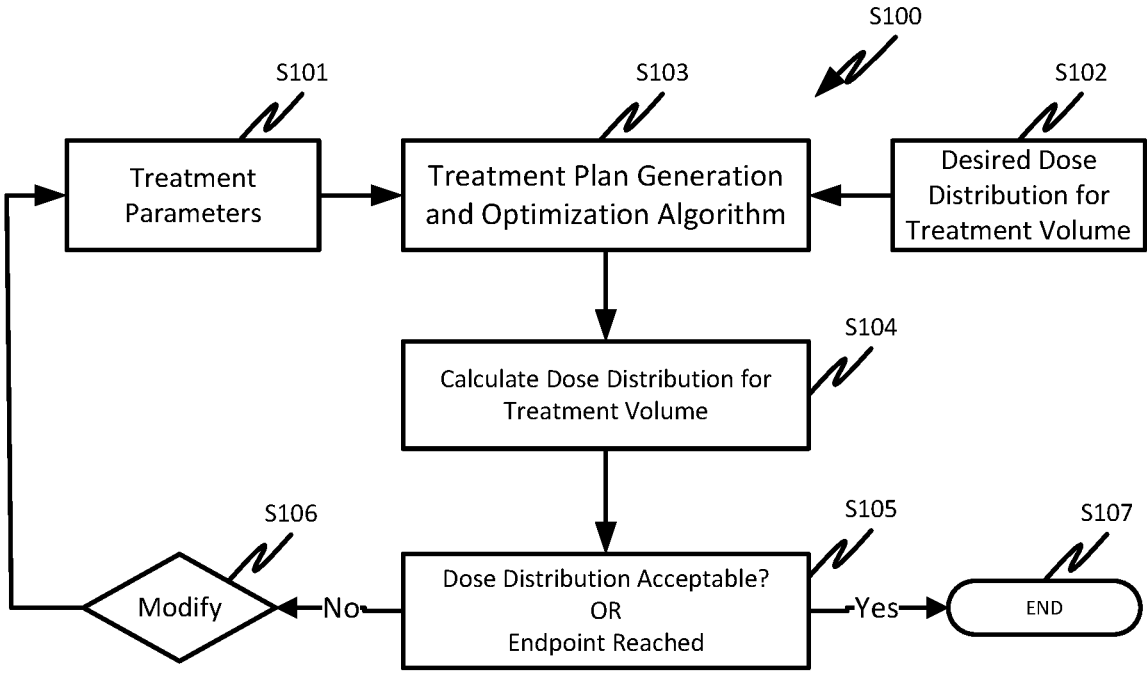
FIG. 3 is a simplified flow diagram for a treatment plan optimization process according to various embodiments of the disclosed subject matter.

Each of these planning algorithms require iterative dose calculations for optimization and generally proceed, as shown in process S100 of FIG. 3. To obtain an optimized treatment plan, the process S100 starts with an initial or base dose calculation using starting treatment parameters S101 for developing the plan. Then, the treatment plan generation and optimization algorithm S103 of the treatment planning module 320 calculates the radiation dose received by each voxel in the treatment volume in S104. If the dose distribution does not conform (S105) to the desired dose distribution (S102) within a predetermined threshold (preset by the physician), the plan is not optimal. In such a case, one or more treatment parameters can be modified (S106), and the dose distribution recalculated in S104. This process is ideally performed iteratively until the desired dose distribution is obtained, at which time the plan is said to be optimized. However, the amount of time needed to perform the large number of calculations for each iteration places a practical limit on the number of iterations that can be performed. As such, generally, the optimization process is terminated at S107 after a predetermined endpoint has been reached. The resulting treatment plan corresponds to the optimized plan.

Due to the search space (i.e., all possible solutions) for system parameters being too large for an optimizer to work with, in current IMRT and VMAT optimization algorithms, the beam geometry (BG) parameters are not optimized during the optimization process S100. Instead, the starting (initial) (BG) parameters, as well as any other values for the (BG) parameters used in the optimization process, are either preset and presented using clinical templates, or are manually entered by the physician/planner/user.

In accordance with the present invention, an optimization process S200 is disclosed that will allow the optimizer to automatically optimize all optimization objectives, namely, optimize all treatment parameters desired to be optimized, including the beam geometry (BG) parameters, to arrive at better quality treatment plans in a short amount of time.

Figure 4:
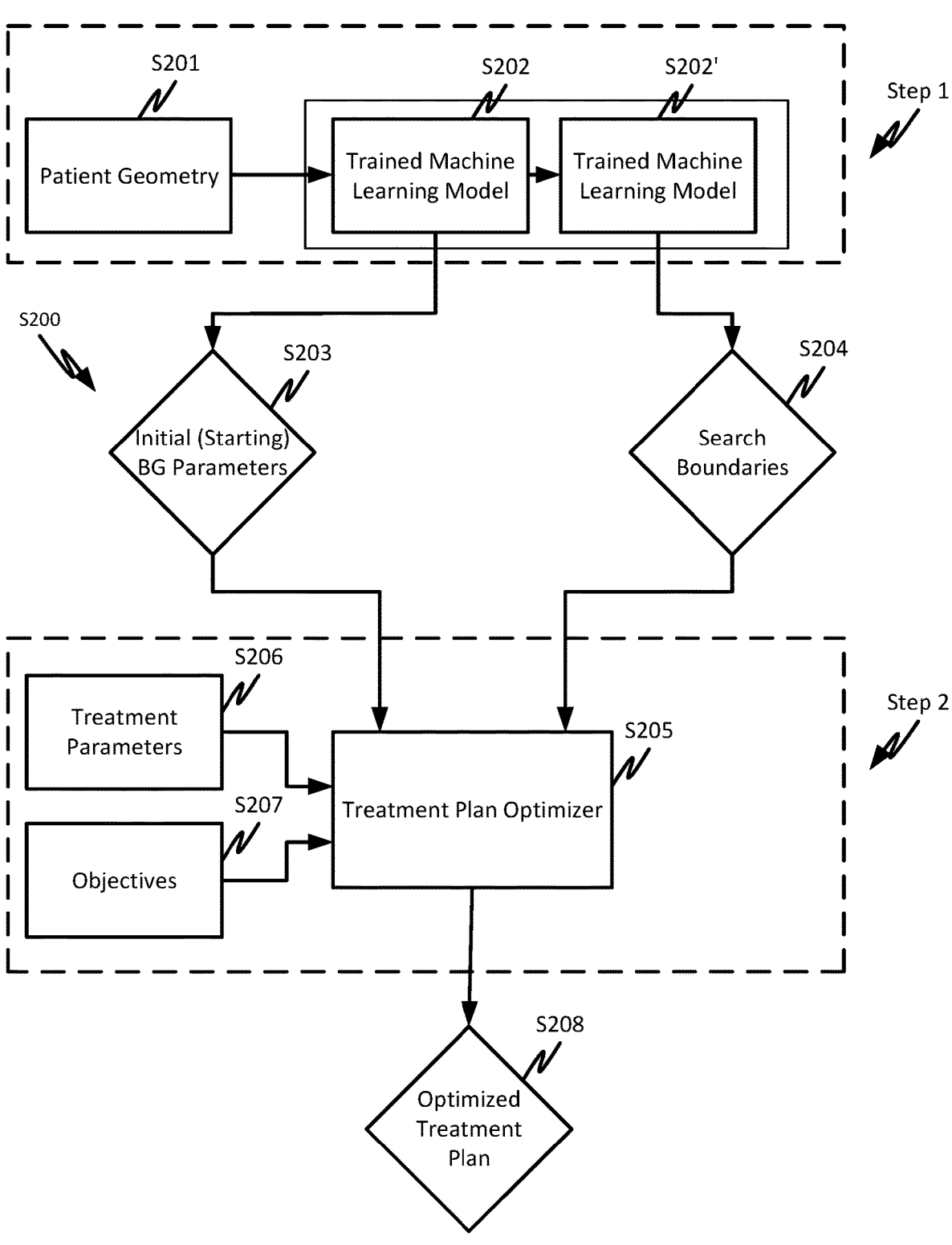
FIGS. 4-5 are schematic flow diagrams for treatment plan optimization processes according to various embodiments of the disclosed subject matter.

An exemplary optimization process S200 is shown in FIG. 4. The optimization process S200 includes two steps, Step 1 and Step 2. In the first step (Step 1), one or more automated processes (S202, S202') may be executed to determine the initial (starting) beam geometry (BG) parameters (S203) and to limit the search space for the beam geometry (BG) parameters (S204) (i.e., automatically finding beam geometry (BG) solutions). The automated process S202 to determine the initial/starting beam geometry (BG) parameters may be independent from the automated process S202' to limit the search space for the beam geometry (BG) parameters. As such, it is to be understood that machine learning models used to predict the initial choice for the beam geometry (BG) parameters may be independent/different from machine learning models used to predict the relevant search ranges for the beam geometry (BG) parameters.

Alternatively, or additionally, some or all of the initial (starting) beam geometry (BG) parameters may be given as templates. For example, beam geometry (BG) parameters templated based on typical patients in a given clinic may be used as the starting/initial beam geometry (BG) parameters. Then, in order to limit the search space for the beam geometry (BG) parameters, a set of rules can be developed to define the search space around the template for the current patient. For example, to cover irradiation of a breast PTV for a current patient, rules may be established for the templated beam geometry (BG) parameters that cover irradiation of the PTV for the current patient while limiting irradiating the contralateral breast and/or the heart, for example. Such rules may include, but are not limited to, rules that limit the gantry and/or collimator angles to angles that avoid irradiating the breast that does not contain the tumor and/or avoid irradiating the heart. These templated (BG) parameters and associated rules to establish search boundaries are exemplary only and it is to be understood that any other appropriate templates and rules may be used to obtain the initial/starting beam geometry (BG) parameters and to establish corresponding search boundaries.

Additionally, or alternatively, a medical personnel (planner) may manually enter one or more of the initial beam geometry (BG) parameters, such as the starting gantry angle, starting collimator angle, etc., and/or the search boundaries for the beam geometry (BG) parameters, via a graphical user interface.

Additionally, or alternatively, the initial/starting beam geometry (BG) parameters may be templated or entered manually by the planner, and an automated process may be applied to establish the search boundaries for the beam geometry (BG) parameters.

In the second step (Step 2), an automated optimization process is executed to optimize all optimization objectives, namely, optimize all variable treatment parameters (S206) including the beam geometry (BG) parameters, based on the information obtained in the first step (Step 1), to generate an optimal treatment plan (S208). Since the search space for the beam geometry (BG) parameters are automatically determined in the first step (Step 1), and since optimization proceeds with all degrees of freedom in the second step (Step 2), optimal treatment plans (S208) are generated faster and are of a higher quality than those where the (BG) parameters are manually set by the physician.

In order to determine the initial/starting beam geometry (BG) parameters (S203), the automated process of the first step (Step 1) uses a trained machine learning model (S202). The machine learning model (S202) is a machine learning model that has been trained to predict beam geometry (BG) parameters as an output based on the patient geometry S201 (i.e., input), the patient geometry S201 including patient related information such as the planning images/image slices (CT, CBCT, MRI, etc.), the body contour, the delineated targets (i.e., target structures), and the delineated OARs.

Figure 6:
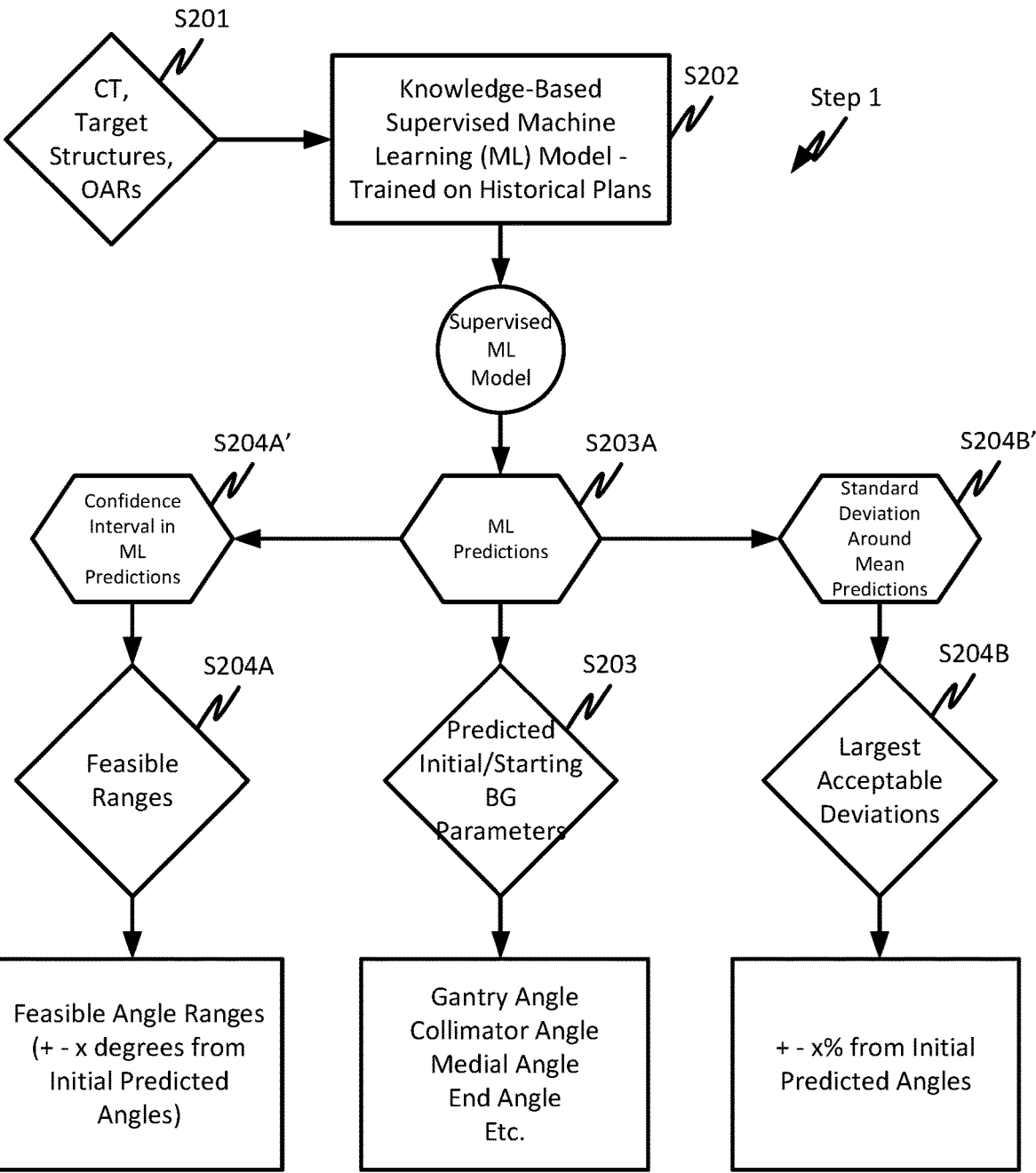
FIGS. 6-7 are schematic flow diagrams for a first step of a treatment plan optimization process according to various embodiments of the disclosed subject matter.

An exemplary trained machine learning model (S202) that can be used in Step 1 is a knowledge-based supervised machine learning model (FIG. 6). The knowledge-based supervised machine learning model S202 shown in FIG. 6 can be a machine learning model that has been trained on historical treatment plans, namely, the machine learning model S202 has been trained to predict beam geometry (BG) parameters for a new patient geometry based on patient geometries and beam geometry (BG) parameters used in previous treatment plans to achieve a same/similar treatment objective.

Figure 5:
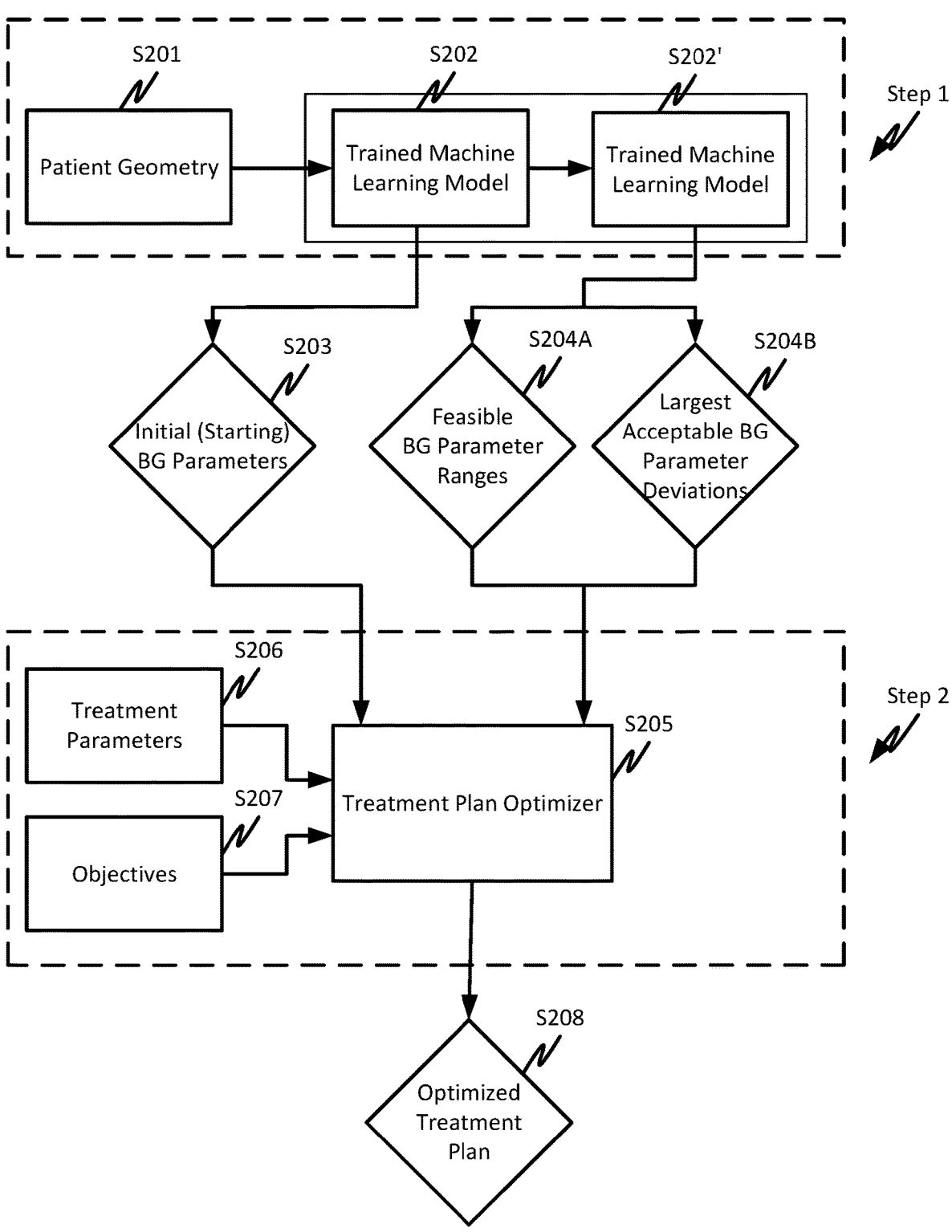

As shown in FIGS. 4 and 5, the patient geometry S201 for which the optimal treatment plan is to be developed, is used as input data in the trained machine learning model S202. By executing the trained machine learning model S202, the initial/starting beam geometry (BG) parameters S203 are obtained as the machine learning model predictions S203A. The output of the trained machine learning model S202 may be used as input to a trained machine learning model S202'. The trained machine learning model S202' is a machine learning model trained to predict the relevant maximum search ranges for the initial/starting beam geometry (BG) parameters S203. By executing the trained machine learning model S202', the confidence interval (S204A') in the machine learning predictions (S203A) and the standard deviations around the mean predictions (S204B') can be determined as the search boundaries S204.

By determining the confidence interval (S204A') in the machine learning predictions (S203A) and the standard deviations around the mean predictions (S204B'), feasible parameter ranges (S204A) for the predictions as well as the largest acceptable deviations from the initial predictions (S204B) can be respectively determined. The feasible parameter ranges (S204A) and the largest acceptable deviations from the initial predictions (S204B) are expressions of the search boundaries S204 for the predicted beam geometry (BG) parameters S203.

Alternatively, or additionally, the search boundaries (i.e., the search ranges) for some or all of the beam geometry (BG) parameters, may be determined using established rules used in clinical practice, and/or determined by the physician. As shown in FIG. 6, when the machine learning model S202 is trained to predict beam geometry (BG) parameters, such as gantry angles, collimator angles, medial angles, etc., the machine learning model outputs the initial/starting gantry angle, collimator angle, medial angle, etc. (S203) as the prediction S203A, from which the corresponding feasible angle ranges S204A and the largest acceptable deviations S204B from the respective initial/starting angles can be calculated and/or determined using an independent machine learning model S202', or using established rules used in clinical practice, and/or determined by the physician.

The initial/starting beam geometry (BG) parameters (S203) and associated search boundaries (S204) obtained in the first step (Step 1), whether expressed as feasible parameter ranges (S204A) or as largest acceptable deviations (S204B), are input into the treatment plan optimizer S205 where the second step (Step 2) commences to find an optimal treatment plan.

Generally, to obtain an optimized treatment plan S208, the optimization process of Step 2 starts with an initial or base dose calculation using the starting treatment parameters S206 of the treatment plan. The initial/starting beam geometry (BG) parameters S203 obtained in the first step (Step 1) are used as the starting beam geometry (BG) parameters. After the initial calculation, the treatment plan generation and optimization module S205 determines whether the treatment objectives S207 are achieved. If the treatment objectives are not achieved, one or more of the treatment parameters, including the beam geometry (BG) parameters, are iteratively modified until the objectives S207 are achieved or an endpoint has been reached. The resulting plan is the optimized treatment plan S208. The search for the beam geometry (BG) parameters are limited to the corresponding search boundaries S204 determined in the first step (Step 1).

Figure 8:
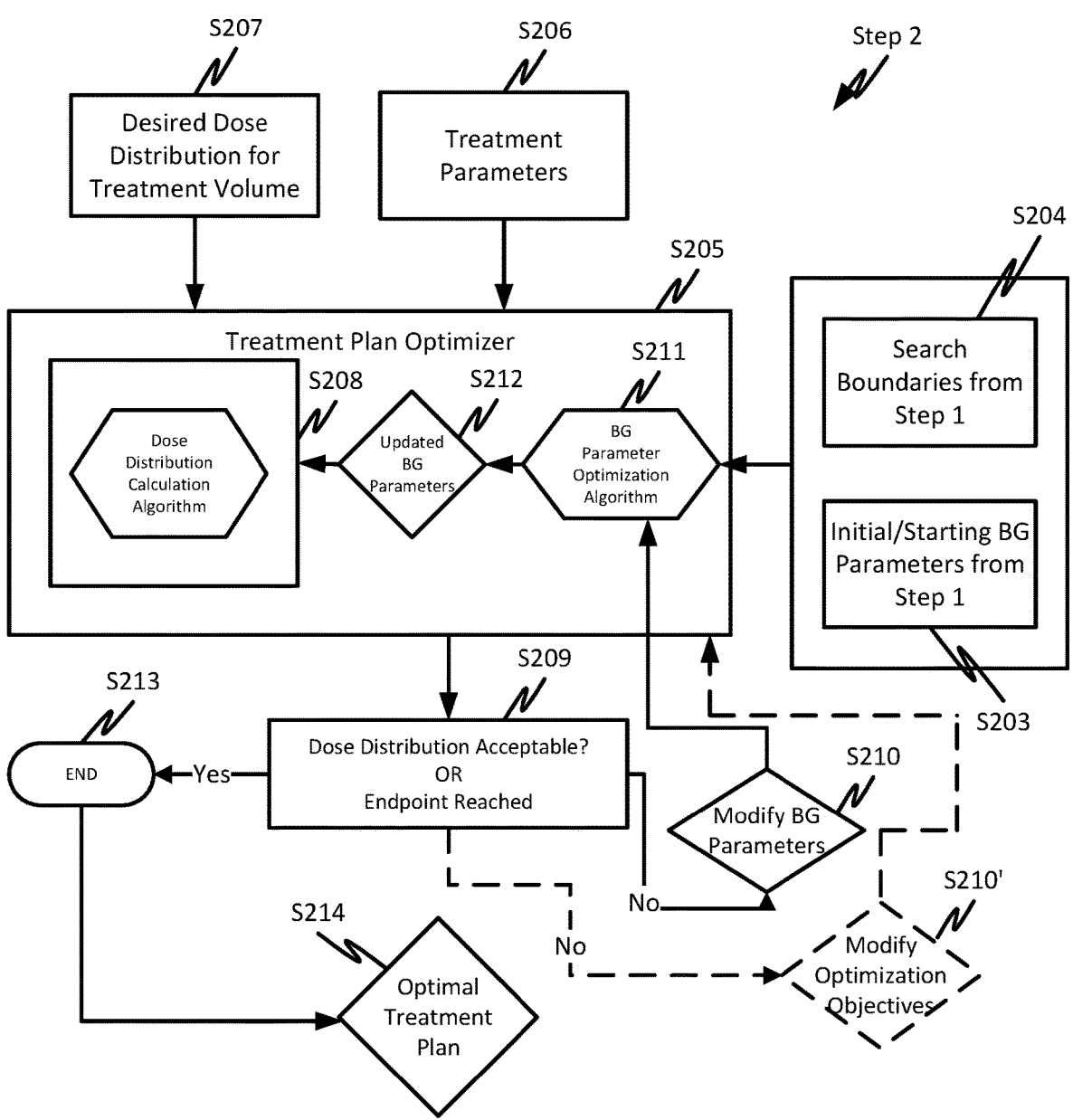
FIG. 8 is a schematic flow diagram for a second step of a treatment plan optimization process according to various embodiments of the disclosed subject matter.

An exemplary optimization Step 2 is illustrated in FIG. 8, where the treatment objective is a desired dose distribution within the treatment volume. The optimization Step 2 starts with an initial or base dose calculation by a dose distribution calculation algorithm S208 using the starting treatment parameters S206 of the treatment plan. The initial/starting beam geometry (BG) parameters S203 obtained in the first step (Step 1) are used as the starting beam geometry (BG) parameters.

If the dose distribution does not conform to the desired dose distribution S207 (i.e., the objective) within a predetermined threshold (preset by the physician), the treatment plan is not optimal. In such a case, one or more of the treatment parameters S206, including the beam geometry (BG) parameters, can be modified, and the dose distribution recalculated at S208. This process is ideally performed iteratively until the desired dose distribution S207 or a preset endpoint is reached at S209, at which time the optimization process of Step 2 is ended at S213 and the resulting treatment plan S214 is said to be optimized.

At each iteration of the optimization process, the beam geometry (BG) parameters are automatically modified at S210 using a beam geometry (BG) parameter optimization algorithm S211 to obtain updated/revised beam geometry (BG) parameters (S212) to be used to recalculate the dose distribution at S208.

Additionally, or alternatively, both the beam geometry (BG) parameters as well as the optimization objectives may be iteratively modified (S210') to generate an optimized treatment plan.

Figures 9A, 9B, 9C:
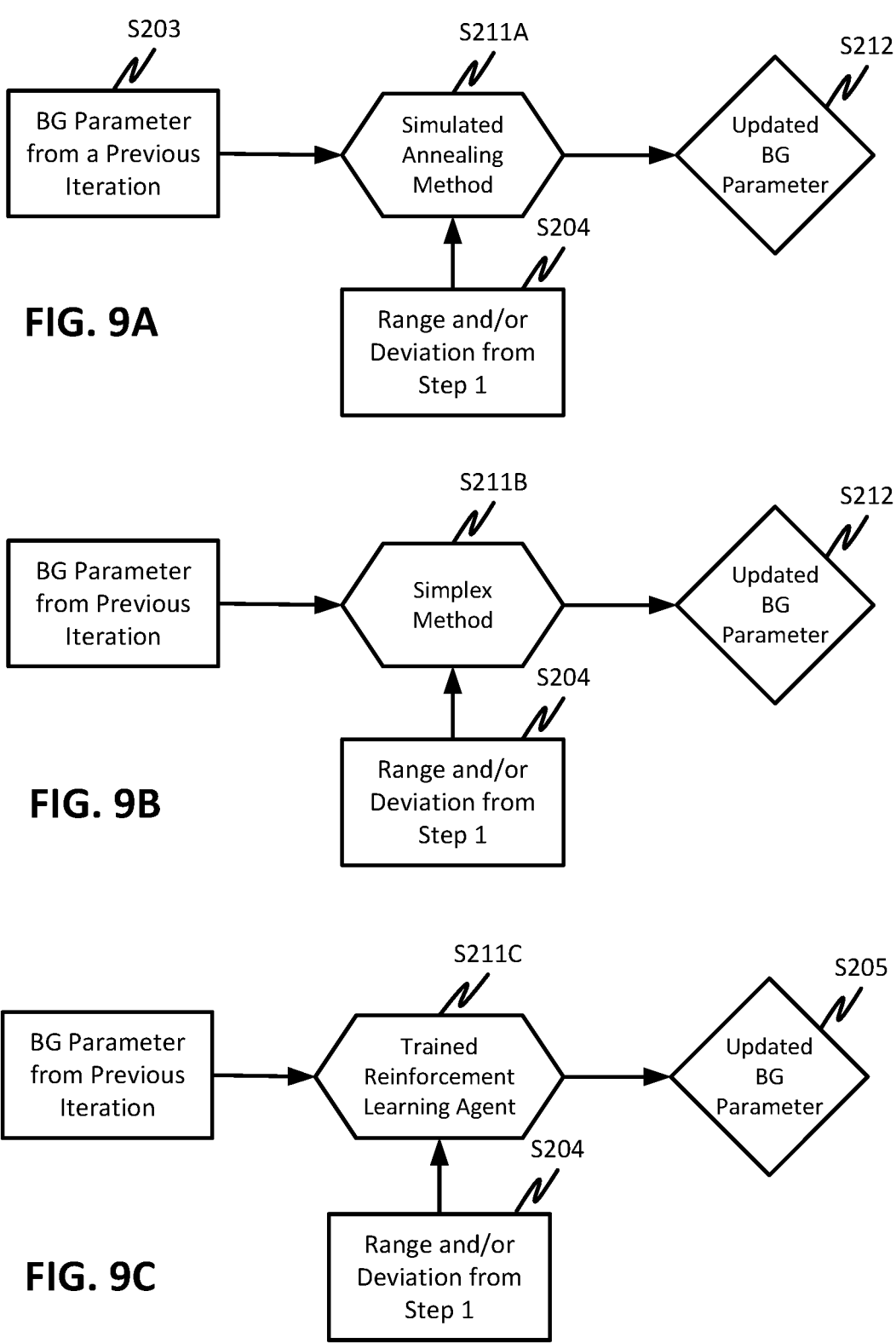
FIGS. 9A-9C are schematic illustration of processes for optimizing beam geometry parameters, according to various embodiments of the disclosed subject matter.

1. FIGS. 9A-9C illustrate exemplary BG parameter optimization algorithms, such as simulated annealing methods S211A, simplex methods S211B, and trained reinforcement learning methods S211C, that can be used to update the beam geometry (BG) parameters at each iteration of the optimization process. Each of these methods S211A-S211C uses the beam geometry (BG) parameter value from a previous iteration of the optimization process, loops through a series of iterations, and arrives at an optimal solution that is within the range/deviation obtained in the first Step 1 for that beam geometry (BG) parameter. For the first optimization iteration, the values for the initial/starting beam geometry (BG) parameters S203 are used in the beam parameter (BG) optimization algorithms S211A-S211C. These are exemplary beam parameter (BG) optimization algorithms only and any other optimization algorithms/methods may be used to update/revise the beam geometry parameters, such as, but not limited to any deterministic, stochastic or heuristic optimization methods.

Figure 7:
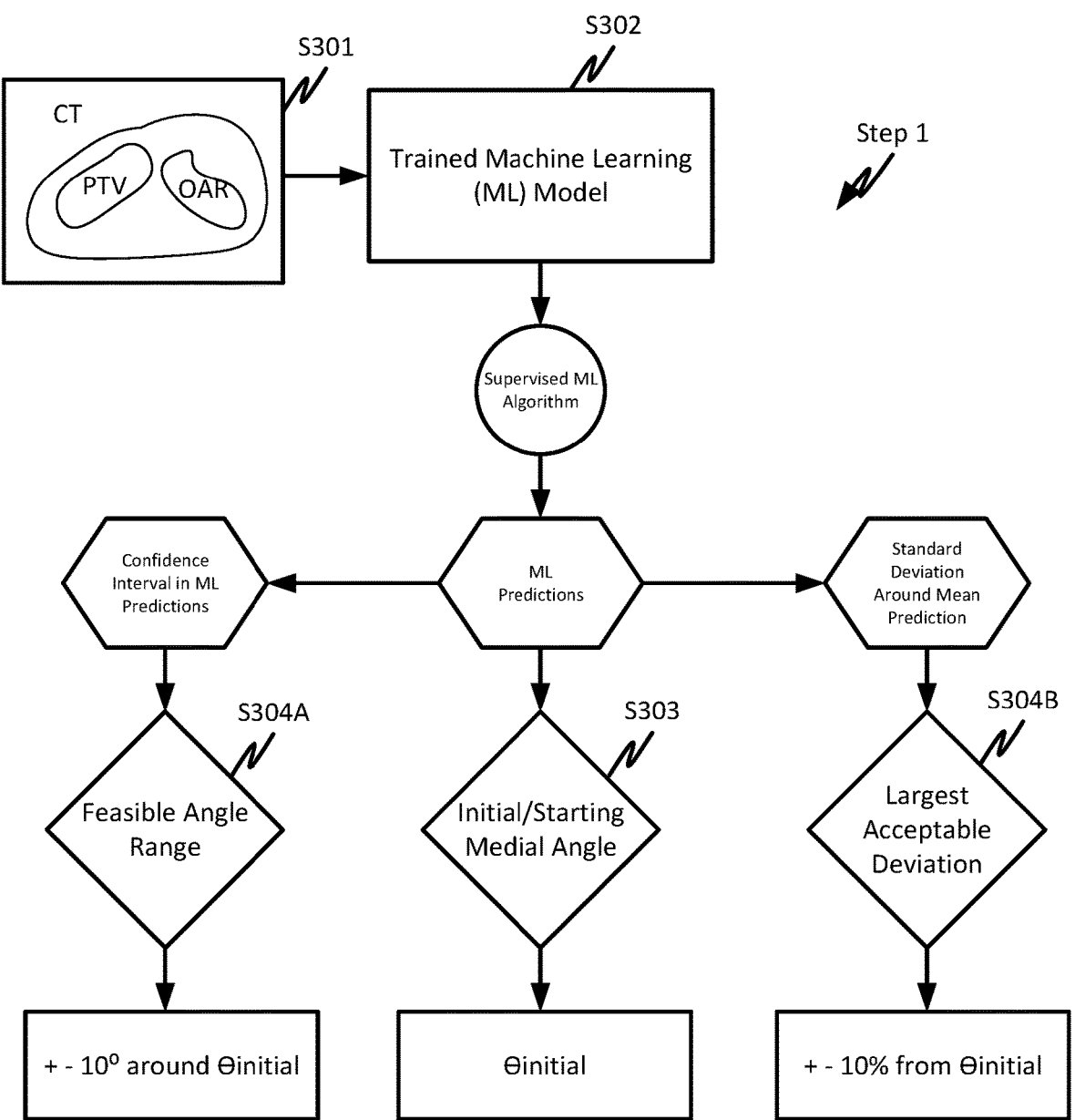

FIG. 7 illustrates an exemplary automated process for developing an optimal treatment plan for irradiating the left-side breast of a patient with partial arc VMAT for non-extended targets. In this example, the body surface is substantially parallel to the chest or breast bone. The relevant beam geometry (BG) parameter that one would like to optimize is the medial angle from which the arc starts. Medial angle is important to adjust to allow maximum coverage of the target (i.e., target structure) while avoiding too much exposure to contra breast and lungs (i.e., OARs). The other beam geometry (BG) parameters, such as the posterior (end angle) and the collimator angle may be templated and/or manually fixed by the physician (planner).

To determine the initial/starting medial angle S303 and the search boundaries (S304A, S304B) for the second optimization Step 2, first a trained machine learning model S302 is executed to predict the initial choice $\theta_{initial}$ for the medial angle S303 from the patient geometry data S301 (i.e., Step 1). The trained machine learning model S302 has been trained on previous treatment plans. The trained machine learning model S302 may further indicate that, for similar cases, the maximum search range (S304A) is not more than ±10 degrees around the initial choice for the medial angle, for example, and/or that the largest acceptable deviation (S304B) is not more than ±10% from the initial choice $\theta_{initial}$ for the medial angle S303, for example. As such, for this exemplary case, the predicted medial angle $\theta_{initial}$ is used as the initial/starting beam geometry (BG) parameter in the second optimization step (Step 2), and $\theta_{initial}\pm10°$ and/or $\theta_{initial}\pm10\%$ is used as the search range for the medial angle within which to find a dosimetrically best treatment plan by the optimizer.

Alternatively, a second, different machine learning model trained to predict the relevant maximum search range for the initial/starting beam geometry (BG) parameters S303 may be applied. By executing this trained machine learning model, the feasible angle range S304A and the largest acceptable deviation S304B may be determined. The predicted medial angle $\theta_{initial}$ is then used as the initial/starting beam geometry (BG) parameter in the second optimization step (Step 2), and $\theta_{initial}\pm10°$ and/or $\theta_{initial}\pm10\%$ is used as the search range for the medial angle within which to find a dosimetrically best treatment plan by the optimizer.

Figure 10:
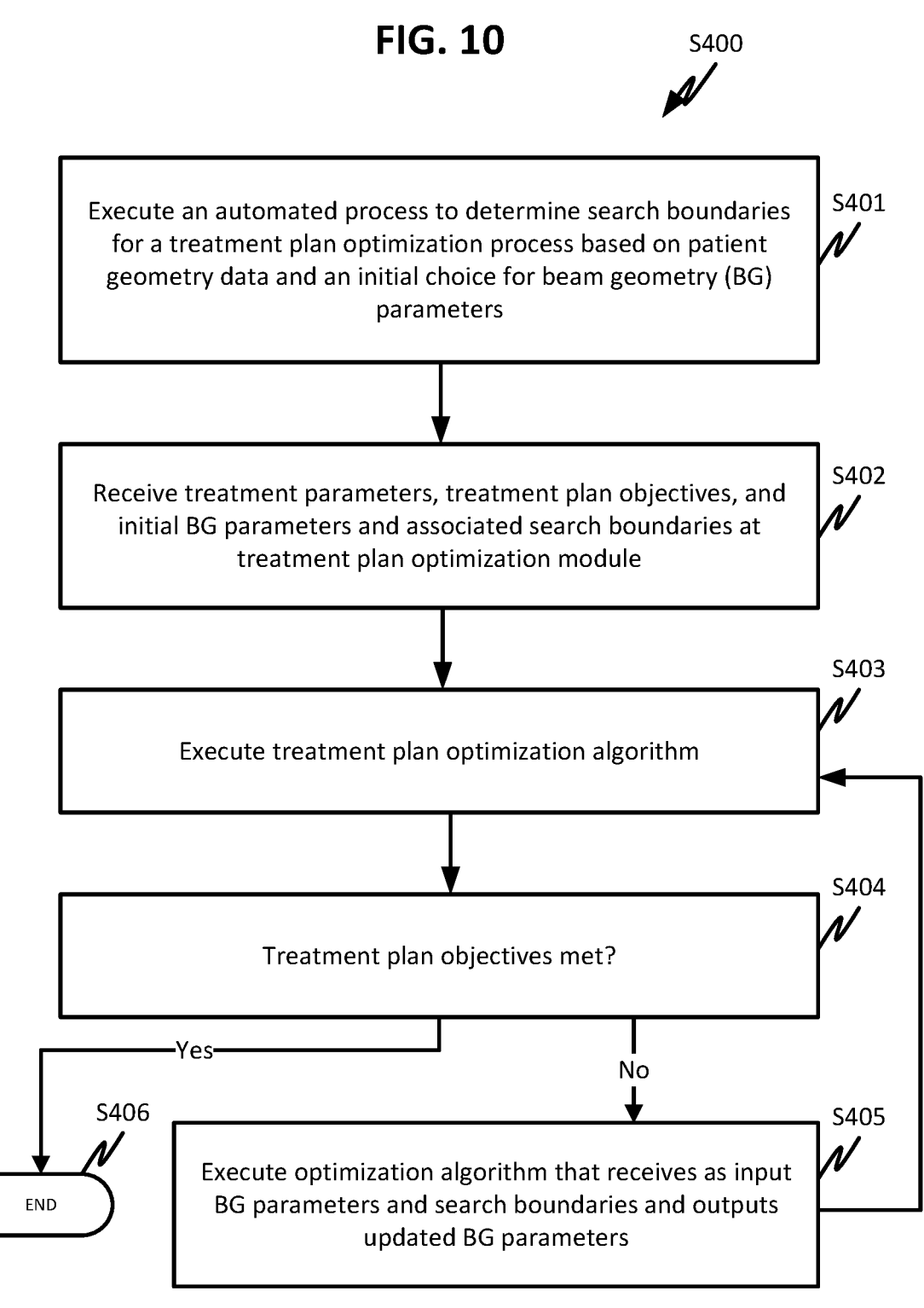
FIG. 10 is a flow diagram of a two-step treatment plan optimization process, according to various embodiments of the disclosed subject matter.

FIG. 10 is a flow diagram showing the steps of an embodiment of a treatment plan optimization process S400 of the instant invention where the optimization proceeds with all degrees of freedom including those related to the (BG) parameters.

In step S401, an automated process is executed to determine search boundaries for beam geometry (BG) parameters based on patient geometry data and an initial choice for the beam geometry (BG) parameters.

In one or more embodiments, the automated process includes executing one or more trained machine learning models to determine the search boundaries for the beam geometry (BG) parameters.

In an exemplary embodiment, the initial choice for the beam geometry (BG) parameters is automatically determined using a trained supervised machine learning model that receives, as input, patient geometry data, and outputs an initial choice for beam geometry (BG) parameters.

In alternative embodiments, the initial choice for the beam geometry (BG) parameters comes from a template or is manually entered by the planner. In such embodiments, the automated process includes executing one or more trained machine learning models that receive, as input, patient geometry data and the initial choice for beam geometry (BG) parameters that was templated or manually entered, and output search boundaries for the beam geometry (BG) parameters. Additionally, or alternatively, the automated process includes executing one or more rules to determine the search boundaries for the beam geometry (BG) parameters. Additionally, or alternatively, the search boundaries for the beam geometry (BG) parameters may also be manually entered by the user.

In step S402, treatment parameters, treatment plan objectives, and the initial beam geometry (BG) parameters and associated search boundaries are received at a treatment plan optimization module.

In step S403, a treatment plan optimization algorithm of the treatment plan optimization module is iteratively executed to optimize the treatment parameters, including the beam geometry (BG) parameters, by automatically modifying/revising/changing the treatment parameters, including the beam geometry (BG) parameters, wherein the search for the beam geometry (BG) parameters is limited to the determined corresponding search boundaries. The treatment parameters, including the beam geometry (BG) parameters are automatically modified/revised/changed at each iteration of the optimization process, until the treatment plan objectives evaluated in Step S404 are determined to be met in S406. The resulting treatment plan is the optimal treatment plan.

The beam geometry (BG) parameters are modified/revised/changed at each iteration of the optimization process by executing an optimization algorithm in S405 that receives the beam geometry (BG) parameters and the corresponding search boundaries as input data and outputs updated beam geometry (BG) parameters that are within the determined corresponding search boundaries.

Thus, by applying a two-step optimization process (Step 1 and Step 2), beam geometry (BG) parameter predictions and acceptable variations are automatically determined (Step 1) and the optimizer is allowed to focus the search around an acceptable initial condition, which improves the optimization algorithm performance.

Figure 11:
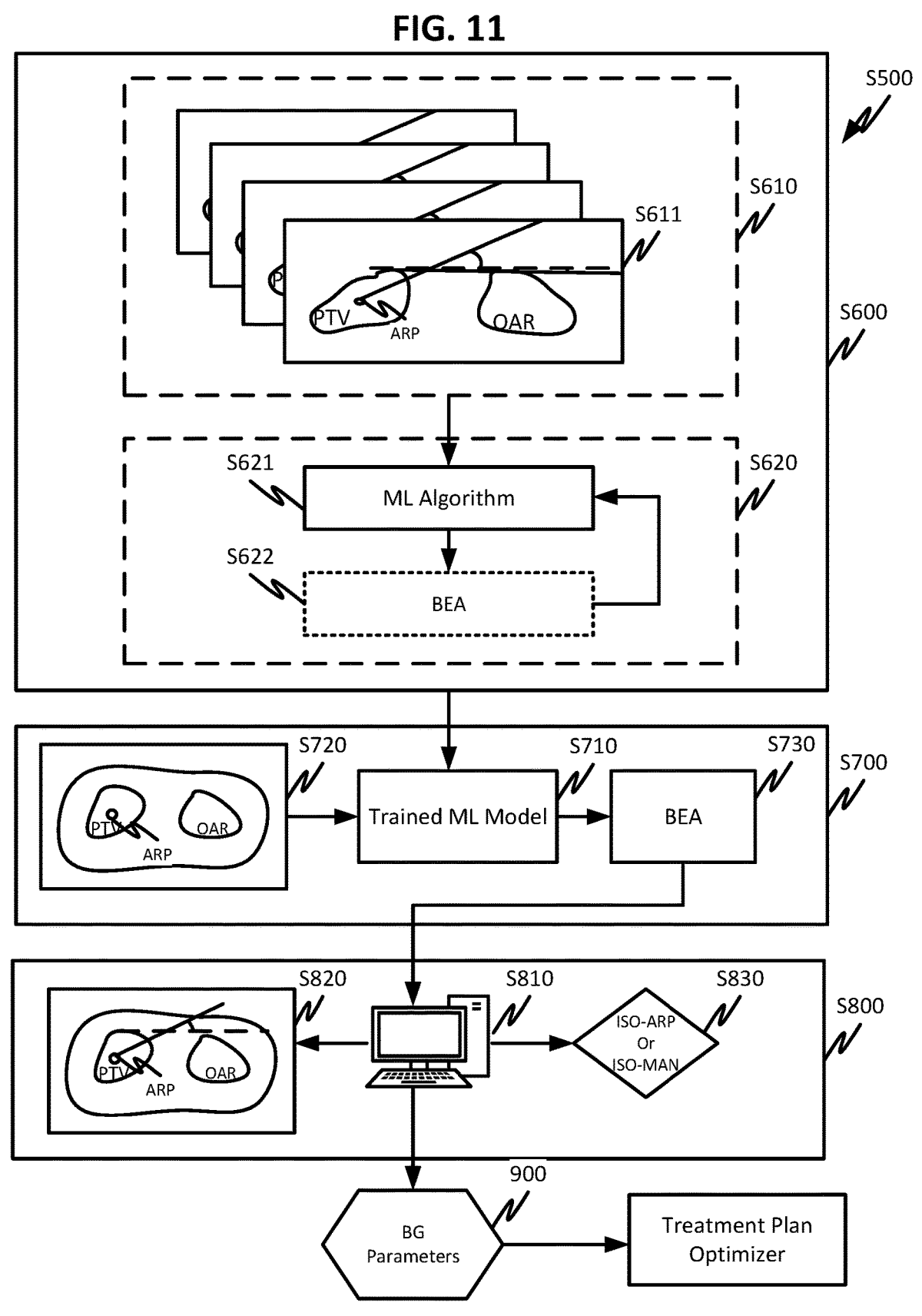
Figure 12:
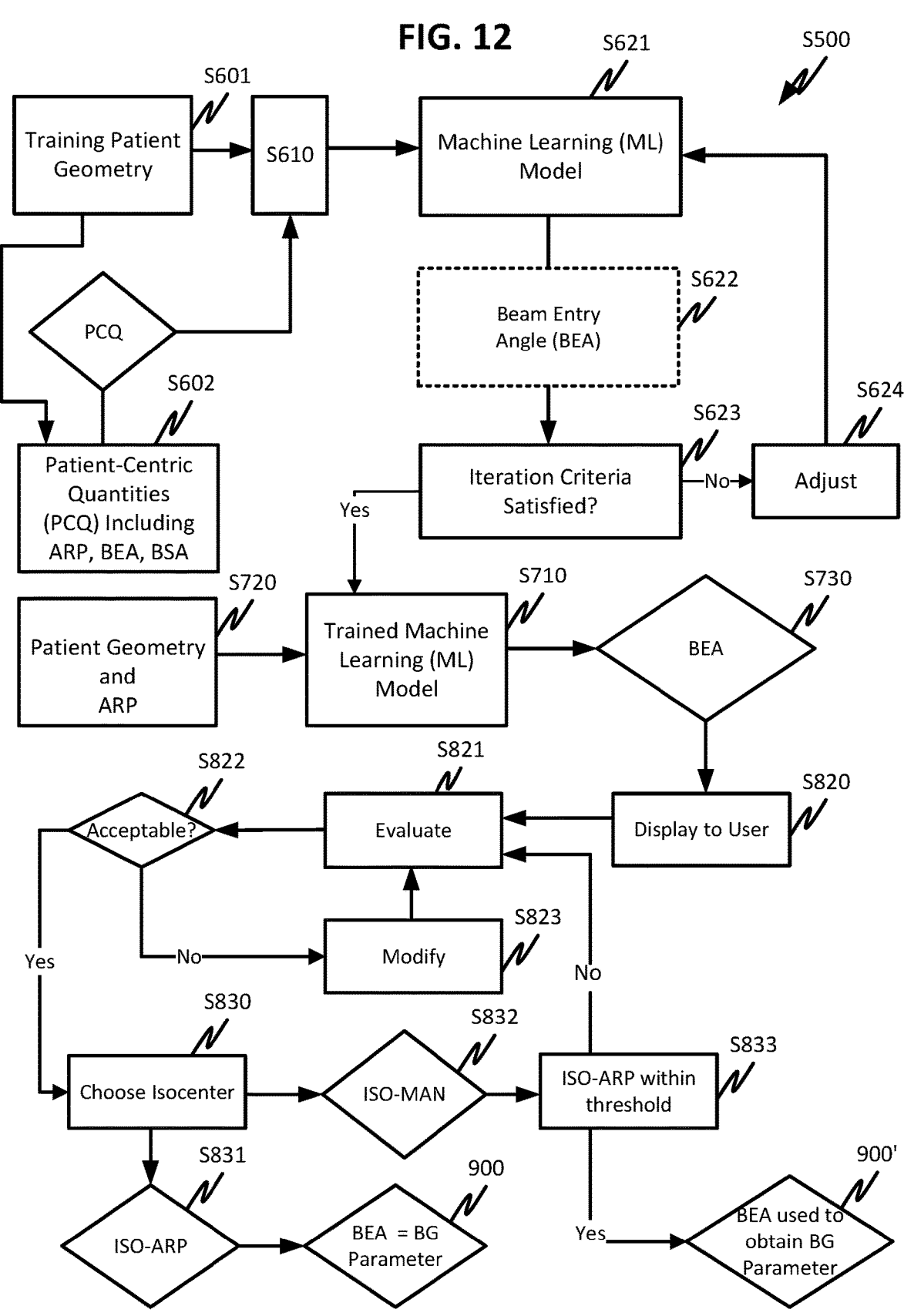

FIGS. 11 and 12 illustrate an example of an automated process S500 to obtain beam geometry (BG) parameters that do not require explicit determination of the system/machine isocenter position to be used in a treatment plan optimization process. Process S500 may include a training phase S600, an application phase S700, and a transformation phase S800.

In the training phase S600, a machine learning model S620 is trained using a training data set S610 to predict a particular output S622. The training data set S610 includes a plurality of images S611 containing patient geometries (target structures (PTV), and OARs) and patient-centric quantities (PCQ) as ground truths.

Figure 13:
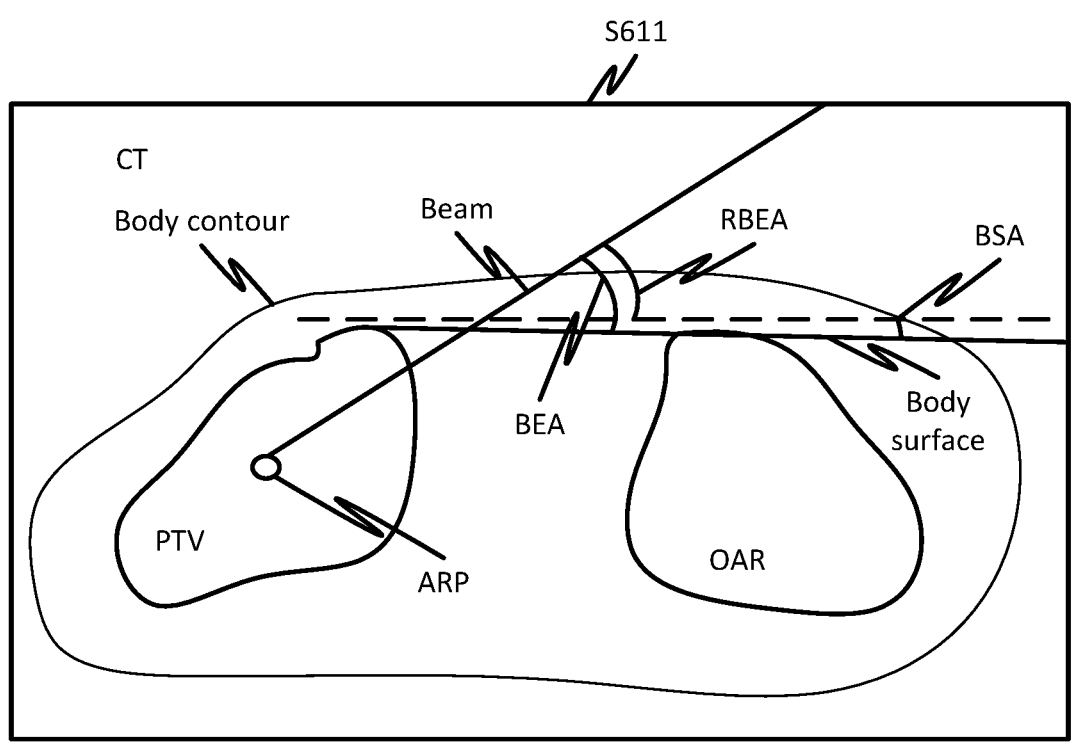
FIG. 13 is an illustration of a patient geometry and patient-centric quantities used to train a machine learning model to predict beam entry angles without explicitly defining a system isocenter.

An exemplary patient image S611 is illustrated in FIG. 13. In this example, the image could be from axial direction of the patient assuming the patient in supine position, but other orientations and views are also possible. Image S611 includes the target structure (PTV), the organ-at-risk (OAR), and patient-centric quantities (PCQs), such as, an auxiliary reference point (ARP), a body surface angle (BSA), a beam entry angle (BEA), and a relative beam entry angle (RBEA). The auxiliary reference point (ARP) is a reference point in the target structure and may be defined as the center of mass of the target. In general, the 'body surface' can be defined using the part of the body contour that is close to the clinical site in question. If, for example, the patient is in supine position and the clinical site is on the upper body (excluding head and neck), the orientation of patient's chest can be used to define the direction of the body surface. The body surface angle (BSA) may be used to track the possibly minor axial tilt of patient's body (i.e., part of the body that is close to the clinical site), as compared with his/her ideal (for example horizontal, depending on the clinical site) position on the treatment couch. The beam entry angle (BEA) may be defined as the angle at which the radiation beam enters the patient with respect to the patient body and target structures, and the relative beam entry angle (RBEA) is the difference between the beam entry angle (BEA) and the body surface angle (BSA).

The training data set S610 may be generated by defining the patient-centric quantities (PCQs) S602 on a plurality of medical images/image slices (CT images, for example) containing the target structures and OARs (S601). The medical images/image slices may be images/image slices previously obtained for the same patient or for previous patients (CT images, for example), and the patient-centric quantities (PCQs) may be user-generated on the images/image slices through observations and experience to facilitate supervised learning. The user may be a planner/physician and/or a qualified medical personnel. Alternatively, or additionally, both the patient geometries and the patient-centric quantities (PCQs) may be user-generated on the medical images/image slices. Alternatively, or additionally, both the patient geometries and the patient-centric quantities (PCQs) may be automatically generated on the medical images/image slices using appropriate contouring/segmentation algorithms for the patient geometries, and graphical algorithms for the patient-centric quantities. The training data set S610 may be stored in the planning image memory, for example.

The machine learning model S621 may be a neural network model that runs on a neural network engine, which refers to any suitable hardware and/or software component of a computer system that is capable of executing algorithms according to any suitable deep learning model. Deep learning models can be based on any existing or later-developed neural networks, or combinations therefor, such as, but not limited to, a convolutional neural network (ConvNet or CNN), residual neural network (ResNet), recurrent neural network (RNN), long short-term memory (LSTM) neural network, recursive neural network, generative adversarial network (GAN), and deep belief network (DBN), for example. Deep neural networks refer to a class of computer-based machine learning algorithms that utilize many layers or stages (i.e., hidden layers) of data processing for feature learning, pattern analysis, and/or classification. In general, deep neural networks are formed by a layered network of processing elements that are interconnected by connections. The layers of nodes are trained from end-to-end (i.e., from input layer to output layer) to extract features from the input and classify a feature(s) to produce an output. For example, nodes in the hidden layers can include a filter or kernel, parameters of which (e.g., kernel weight, size, shape, or structure) can be adjusted during the training process. The training of the machine learning model S620 refers to determining one or more parameters of nodes in the hidden layers of the deep neural network by an iterative process S623 that varies parameters S624 such that the neural network model output S622 more closely matches corresponding ground truths. In the instant case, the machine learning model S621 is trained to output a beam entry angle (BEA) S622 that closely matches the ground truth beam entry angles (BEAs) of the training data set S610.

In operation, the training data set S610 is input to the machine learning model S621, for example, to its input layer. The machine learning model S621 processes the training data by propagating though nodes of its hidden layers to produce an outcome, namely a beam entry angle (BEA) S622, at its respective output layer. This output beam entry angle BEA (S622) is compared to the ground truth beam angle (BEA) via a loss function. The loss function may be a mean-squared error, dice loss, cross entropy-based loss or any other loss function known in the art. During the training S600, the machine learning model S621 is given feedback by the loss function on how well its output S622 matches the correct output (ground truth BEA). Once the iteration criteria S623 is satisfied (i.e., the loss function meets a predetermined threshold, a threshold number of iterations has been reached, or no further improvement is seen between iterations), the machine learning model is fixed as the trained machine learning model S710. Otherwise, the training S600 proceeds by adjusting S624 parameters of the hidden layer nodes in order to improve the match between the output (S622) and the desired output (i.e., ground truth BEA). The training process S600 can iterate repeatedly until the desired iteration criteria is satisfied at S623.

Once the training phase S600 has been completed, the process S500 can proceed to the application phase S700, which uses the trained machine learning model S710 to process images of the patient to automatically predict beam entry angles (BEAs) relative to the patient. The application phase S700 can begin where a patient data set S720 is provided to the trained machine learning model S710. The patient data set S720 includes one or more images/image slices (CT, for example) obtained for the patient, each containing the target structure (PTV) and OAR (i.e., patient geometry) as well as an auxiliary reference point (ARP) defined for the target structure (PTV). The auxiliary reference point (ARP) may be the center of the mass of the target and may be determined by a user or automatically calculated using a center of mass calculation algorithm. Any appropriate center of mass calculation algorithms may be used to find the center of mass of the target.

The trained machine learning model S710 takes the patient data set S720 including the patient geometry and associated auxiliary reference point (ARP) as input, processes the data set S720, and outputs beam entry angles (BEAs) S730 based on its training.

In the transformation phase S800, the beam entry angles (BEAs) S730 obtained in the application phase S700 can be overlaid S820 on the anatomical structures contained in the CT images used in the application phase S700 using a computer processing device S810, so as to allow the user to visualize the predicted beam entry angles (BEAs) S730 with respect to the patient geometry. The predicted beam entry angles (BEAs) S730 overlaid on the patient geometry including the body contour, target structures and OARs, can be displayed (S820) on a display of the computer processing device S810. The computer processing device S810 may be the same or a different computer processing device than the computer processing device 310 used in treatment planning, the machine learning model training, or the computer processing device 200 of the treatment system 100. When different computer processing systems are used, the computer processing systems are networked with each other and the controller 200 via I/O 210.

The beam entry angles (BEAs) overlaid on the patient geometry are next evaluated by the user (S821). The beam entry angles (BEAs) S730 may be interactively manually adjusted/tuned (S823) by the user until the user determines in S821 that the beam entry angles (BEAs) are acceptable (S822). The determination may be based on the visual observation of the predicted beam entry angles (BEAs) relative to the target structure, the OAR, and the auxiliary reference point (ARP) in the target structure. The evaluation may be guided by the user's clinical experience with acceptable beam entry angles relative to patient's geometries. The computer processing device S810 can include a graphical interface to allow for the interactive beam entry angle (BEA) tuning/adjustment.

Once the beam entry angles (BEAs) are accepted, the user can proceed to define the isocenter in S830 by either accepting the auxiliary reference point (ARP) of S820 as the isocenter (ISO-ARP) in S831 or by manually entering an isocenter location (ISO-MAN) based on the observed ARP location (S832). Instead of manually choosing the isocenter, the isocenter may be picked using a computer processing algorithm programmed to define a best possible location for an isocenter based on the patient geometry and the auxiliary reference point (ARP).

If the user chooses the auxiliary reference point (ARP) (S831) as the isocenter, the beam entry angles (BEAs) accepted in S822 are determined to be the beam geometry (BG) parameters 900. In a particular embodiment, the beam geometry (BG) parameters 900 are the gantry angles, and as such, the beam entry angles (BEAs) accepted in S822 are the same as the gantry angles.

If the user manually (or using the algorithm) chooses the isocenter (ISO-MAN), the isocenter is further evaluated in S833 to determine whether the chosen (or calculated) isocenter location is close to the auxiliary reference point (ARP). The evaluation can be done by displaying the isocenter location on the patient geometry and visually determining whether the isocenter location is close to the auxiliary reference point (ARP), or by calculating the difference between the isocenter location and the auxiliary reference point (ARP) location using the computer processing system S810.

If a determination is made in S833 that the ISO-MAN (S832) is close to the auxiliary reference point (ARP) (i.e., within a predetermined threshold), the beam geometry (BG) parameters 900' are determined from the beam entry angles (BEAs). For example, the beam entry angles (BEAs) accepted in S822 can be further modified (S823) to account for the difference between the location of the auxiliary reference point (ARP) and the location of the ISO-MAN (S832). The modified beam entry angles (BEAs) are then accepted as the beam geometry (BG) parameters 900'. Thus, when the ISO-MAN (S832) is close to the auxiliary reference point (ARP) (i.e., is within a predetermined threshold), the gantry angles 900' can also be determined from the beam entry angles (BEAs).

If, on the other hand, a determination is made in S833 that the ISO-MAN (S832) is far from the auxiliary reference point (ARP) (i.e., outside of the predetermined threshold), and thus, clearly outside of the target, the user may need to re-evaluate whether the (BEAs) predicted in S730 are in fact acceptable approximations for allowed beam geometry (BG) parameters (i.e., gantry angles) considering the specific isocenter choice (ISO-MAN). This can be done by manually re-evaluating the beam geometry in S821 and repeating the process until acceptable (BEAs) and subsequently, acceptable beam geometry (BG) parameters (900') are obtained.

Figure 14:
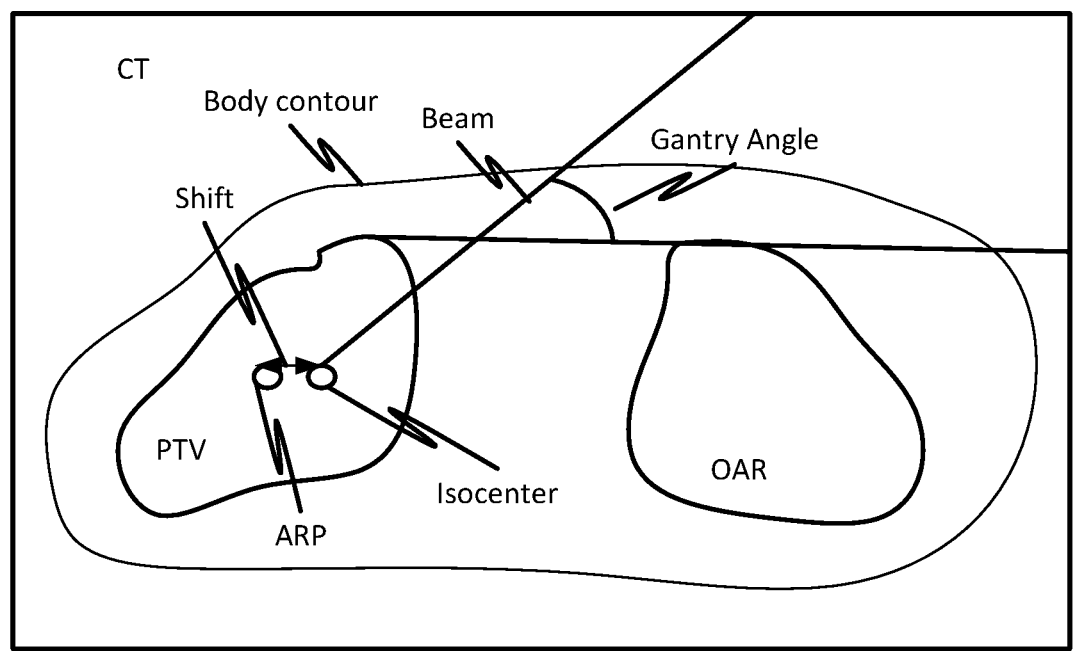
FIG. 14 is a display of a gantry angle predicted using an automated process to predict beam geometry parameters without explicitly defining a system isocenter.

Optionally, once the isocenter (ISO-ARP S831 or ISO-MAN S832) and the gantry angles (900, 900') are defined, the patient and machine setup can be revisualized similarly to FIG. 13 and displayed to the user. The body contours and target structures may be appropriately shifted relative to the determined isocenter and the gantry directions drawn on the display, as shown in FIG. 14, for example. The user may accept, reject or manually tune the gantry angles, as was done for the beam entry angles (BEAs). After a final check, the machine-specific beam geometry (BG) parameters (i.e., gantry angles) may be accepted as beam geometry (BG) parameters for treatment planning.

The beam geometry (BG) parameters 900, 900' are machine-specific parameters that can be used in treatment planning. In an exemplary embodiment, the beam geometry (BG) parameters 900, 900' obtained in the process S500 can be used as the initial/starting beam geometry (BG) parameters in the two-step optimization process S200.

FIG. 15 illustrates an exemplary flow diagram showing the steps of a process S1000 that allows for automatic prediction of beam geometry (BG) parameters that a user can evaluate and optionally adjust without needing to define the explicit isocenter at the beginning of the process.

In step S1001, a computer processing system receives training patient geometry data (CT images with delineated target structures and OARs). In step S1002, patient-centric quantities including auxiliary reference points inside the target structures, body surface angles, and beam entry angles are defined for the training patient data. In step S1003, a machine learning model is trained using the training patient geometry data and the patient-centric quantities to predict beam entry angles (BEA). In step S1004, the computer processing system receives patient geometry data including a medical image (CT, for example) including the body contour, target structure and OAR, and determines an auxiliary reference point (ARP) within the target structure. In step S1005, the patient geometry and the associated ARP are used as input to a trained machine learning model that predicts a beam entry angle (BEA) as the output. In step S1006, the predicted beam entry angle (BEA) is superimposed on the patient geometry and displayed to a user. In step S1007, the user accepts, rejects or tunes the beam entry angle (BEA). In step S1008, the user determines the isocenter by either accepting the ARP as the isocenter or manually (or using an algorithm) setting up the isocenter. In step S1009, a machine specific beam geometry (BG) parameter (gantry angle) is determined based on the chosen isocenter. Optionally, in step S1010, the body contour and target structures are shifted relative to the chosen isocenter and the gantry angle is drawn on the display, followed by S1011 where the user can again accept, reject or tune the gantry angle.

The accepted gantry angle can optionally be used in S1012 as the initial beam geometry (BG) parameter for treatment planning and optimization in step S1013.

Software stored in the planning image memory and/or computer 310 of the treatment planning system 300 and/or the computer used in S810 is configured to be loaded and processed in any conventional manner, and is configured to be executed in order to optimize a treatment plan, train and apply trained machine learning models, determine patient-centric quantities, and predict, evaluate, and adjust beam entry angles without specifically defining the system/machine isocenter, as described throughout this specification. The software is further configured to optimize the treatment plan for irradiating a target volume using a radiotherapy system having a multileaf collimator and is capable of irradiating the treatment volume from one or a plurality of angles.

The treatment planning software further includes software for translating the results of the optimized treatment plan into instructions for operating the radiation therapy system 100 for controlling the elements of the radiation therapy system 100 that define the beam geometry and angle of irradiation (treatment couch, gantry, MLC, etc.) in order to deliver the optimized radiation treatment plan to the patient 110.

It is thus apparent that methods and systems are disclosed herein for automated treatment plan optimization processes that can proceed with all degrees of freedom including those related to beam geometry (BG) parameters.

It is also apparent that methods and systems are disclosed herein for determining automated beam geometry (BG) parameters (i.e., finding BG solutions) that do not require explicit determination of the system isocenter position.

It is also apparent that systems including a computer processing device configured to execute a sequence of programmed instructions embodied on a computer-readable storage medium, the execution thereof causing the system to execute any or alternatively a combination of any of the method steps disclosed herein, are also disclosed.

A non-transitory computer-readable storage medium upon which is embodied a sequence of programmed instructions for a treatment plan optimization and a computer processing system that executes the sequence of programmed instructions embodied on the computer-readable storage medium are also disclosed. Execution of the sequence of programmed instructions can cause the computer processing system to execute the treatment plan optimization processes described herein.

A non-transitory computer-readable storage medium upon which is embodied a sequence of programmed instructions for determining automated beam geometry (BG) parameters (i.e., finding BG solutions) that do not require explicit determination of the system isocenter position, and a computer processing system that executes the sequence of programmed instructions embodied on the computer-readable storage medium are also disclosed.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method for optimizing a treatment plan for a radiation beam delivery system, the method comprising:
   a first step configured to limit a search space for an optimization objective of an optimization algorithm, the optimization objective being a beam geometry (BG) parameter of the radiation beam delivery system; and
   a second step configured to optimize the beam geometry (BG) parameter based on the limited search space obtained in the first step without explicit determination of the radiation beam delivery system isocenter.

2. The method of claim 1, wherein the first step includes one of: predicting an initial choice for the beam geometry (BG) parameter, inputting, by a user, the initial choice for the beam geometry (BG) parameter, or using a template to enter the initial choice for the beam geometry (BG) parameter, wherein the predicting of the initial choice for the beam geometry (BG) parameter includes executing a machine learning model that is trained to predict the initial choice for the beam geometry (BG) parameter based on patient geometry.

3. The method of claim 2, wherein the first step further includes one of: predicting a feasible range for the beam geometry (BG) parameter and/or a largest acceptable deviation from the initial choice for the beam geometry (BG) parameter, inputting, by the user, a feasible range for the beam geometry (BG) parameter and/or a largest acceptable deviation from the initial choice for the beam geometry (BG) parameter, or templating a feasible range for the beam geometry (BG) parameter and/or a largest acceptable deviation from the initial choice for the beam geometry (BG) parameter.

4. The method of claim 3, wherein the beam geometry (BG) parameter includes one of a gantry angle, a collimator angle, and a radiation field direction of the radiation beam delivery system.

5. The method of claim 3, wherein the second step includes:

receiving, as input to the treatment plan optimization algorithm, information regarding desired dose distribution within a treatment volume of a patient, and treatment parameters;

calculating dose distribution within the treatment volume by executing the treatment plan optimization algorithm;

determining whether the calculated dose distribution is within an acceptable threshold of the desired dose distribution; and iteratively modifying one or more of the treatment parameters including the beam geometry (BG) parameter until the calculated dose distribution is within the acceptable threshold or an endpoint has been reached, wherein the beam geometry (BG) parameter is modified based on the search space obtained in the first step.

6. The method of claim 5, wherein the beam geometry (BG) parameter is modified at each iteration of the optimization process using one of a trained reinforcement learning agent, a simplex method, a simulated annealing method, or any other deterministic, stochastic or heuristic optimization method.

7. The method of claim 2, wherein the machine learning model is a knowledge-based supervised machine learning model trained using historical treatment plans.

8. The method of claim 1, wherein the optimization step includes executing an automated process to predict an initial choice for the beam geometry (BG) parameter without explicit determination of the radiation beam delivery system isocenter.

9. The method of claim 8, wherein the automated process includes: executing a trained machine learning model to predict, based on patient geometry as input, a beam entry angle relative to a reference point in the patient; and determining the initial beam geometry (BG) parameter based on the predicted beam entry angle.

10. The method of claim 9, wherein the determining of the initial beam geometry (BG) parameter includes:

displaying the predicted beam entry angle superimposed on the patient geometry on a display for evaluation by a user;

allowing the user to accept the predicted beam entry angle or interactively modify the predicted beam entry angle on the display until an acceptable beam entry angle is obtained; and allowing the user to accept the reference point as the isocenter or manually enter an isocenter, wherein the accepted beam entry angle is chosen as the initial beam geometry (BG) parameter when the reference point is accepted as the isocenter, and the initial beam geometry (BG) parameter is calculated from the accepted beam entry angle when the manually entered isocenter is in close proximity to the reference point.

11. The method of claim 10, wherein the patient geometry includes a body contour and a target structure, the reference point is the center of mass of the target structure, and the beam geometry (BG) parameter is a gantry angle.

12. The method of claim 11, further comprising:

shifting the body contour and the target structure relative to the determined isocenter; and further adjusting the gantry angle based on the shift.

13. An automated method for obtaining beam geometry (BG) parameters for treatment planning without explicit determination of an isocenter of a radiation beam delivery system delivering the treatment plan to a patient, the method comprising:

determining a reference point within the target;

obtaining a predicted beam entry angle relative to the reference point by executing a machine learning model trained to predict, based on patient geometry, the beam entry angle relative to the reference point;

displaying the predicted beam entry angle superimposed on the patient geometry for evaluation by a user;

allowing the user to accept the predicted beam entry angle or to interactively modify the predicted beam entry angle until an acceptable beam entry angle is obtained; and allowing the user to accept the reference point as the isocenter or manually enter an isocenter, wherein the accepted beam entry angle is chosen as the beam geometry (BG) parameter when the reference point is accepted as the isocenter, and the beam geometry (BG) parameter is calculated from the accepted beam entry angle when the manually entered isocenter is in close proximity to the reference point.

14. The method of claim 13, wherein the patient geometry includes a body contour and a target structure, the reference point is a center of mass of the target structure, and the beam geometry (BG) parameter is a gantry angle.

15. The method of claim 14, further comprising:

shifting the body contour and the target structure relative to the determined isocenter; and further adjusting the gantry angle based on the shift.

16. A system for developing a treatment plan for the delivery of a prescribed radiation dose to a treatment volume within a patient, comprising:

a processor; and a memory coupled to the processor, the memory including instructions that when executed by the processor cause the processor to:

receive information related to the prescribed radiation dose, the treatment volume, and a plurality of parameters associated with the radiation beam delivery system, the plurality of parameters including a beam geometry (BG) parameter;

develop a treatment plan optimization model based on the received information, the treatment plan optimization model being configured to find an optimal dose distribution within the treatment volume; and generate an optimal treatment plan based on the treatment plan optimization model, wherein the generating of the optimal treatment plan includes:

a first step configured to limit a search range for the beam geometry (BG) parameter; and a second step configured to optimize the treatment parameters, wherein the beam geometry (BG) parameter is optimized based on the limited search field obtained in the first step and without explicit determination of an isocenter of a system used for the radiation dose delivery.

17. The system of claim 16, wherein the first step includes one of: predicting, inputting by a user, or using a template to determine an initial choice for the beam geometry (BG) parameter and a feasible range for the beam geometry (BG) parameter and/or a largest acceptable deviation from the initial choice for the beam geometry (BG) parameter, wherein the predicting includes executing a trained machine learning model to predict, based on patient geometry as input, the initial choice for the beam geometry (BG) parameter.

18. The system of claim 17, wherein the second step includes:

calculating dose distribution within the treatment volume;

determining whether the calculated dose distribution is within an acceptable threshold of the desired dose distribution; and iteratively modifying one or more of the treatment parameters including the beam geometry (BG) parameter until the calculated dose distribution is within the acceptable threshold or an endpoint has been reached, wherein the beam geometry (BG) parameter is modified based on the search range obtained in the first step.

19. The system of claim 18, wherein the beam geometry (BG) parameter is modified using one of a trained reinforcement learning agent, a simplex method, a simulated annealing method, or any other deterministic, stochastic or heuristic optimization method.

20. A system for obtaining beam geometry (BG) parameters for treatment planning without explicit determination of an isocenter of a radiation beam delivery system delivering the treatment plan to a patient, the system comprising:

a processor; and a memory coupled to the processor, the memory including instructions that when executed by the processor cause the processor to:

determine a reference point within the target;

obtain a predicted beam entry angle relative to the reference point by executing a machine learning model trained to predict, based on patient geometry, the beam entry angle relative to the reference point;

display the predicted beam entry angle superimposed on the patient geometry for evaluation by a user;

allow the user to accept the predicted beam entry angle or to interactively modify the predicted beam entry angle until an acceptable beam entry angle is obtained; and allow the user to accept the reference point as the isocenter or manually enter an isocenter, wherein the accepted beam entry angle is chosen as the beam geometry (BG) parameter when the reference point is accepted as the isocenter, and the beam geometry (BG) parameter is calculated from the accepted beam entry angle when the manually entered isocenter is in close proximity to the reference point, the processor being further configured to:

shift the patient geometry relative to the determined isocenter; and further adjust the gantry angle based on the shift.

* * * * *